(12) United States Patent
Yeung et al.

(10) Patent No.: US 10,898,538 B2
(45) Date of Patent: Jan. 26, 2021

(54) METHODS FOR MAINTAINING PEGYLATION OF POLYPEPTIDES

(71) Applicant: BRISTOL-MYERS SQUIBB COMPANY, Princeton, NJ (US)

(72) Inventors: Bernice Yeung, Lexington, MA (US); Jack Wang, Lexington, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 270 days.

(21) Appl. No.: 15/253,358

(22) Filed: Aug. 31, 2016

(65) Prior Publication Data

US 2017/0049905 A1    Feb. 23, 2017

Related U.S. Application Data

(63) Continuation of application No. 14/117,458, filed as application No. PCT/US2012/037908 on May 15, 2012, now abandoned.

(60) Provisional application No. 61/487,027, filed on May 17, 2011.

(51) Int. Cl.
| | | |
|---|---|---|
| A61K 38/02 | (2006.01) | |
| A61K 47/60 | (2017.01) | |
| A61K 47/64 | (2017.01) | |
| C07K 14/78 | (2006.01) | |

(52) U.S. Cl.
CPC .............. *A61K 38/02* (2013.01); *A61K 47/60* (2017.08); *A61K 47/6435* (2017.08); *C07K 14/78* (2013.01)

(58) Field of Classification Search
None
See application file for complete search history.

(56) References Cited

U.S. PATENT DOCUMENTS

| | | |
|---|---|---|
| 4,002,531 A | 1/1977 | Royer |
| 5,382,657 A | 1/1995 | Karasiewicz et al. |
| 5,514,581 A | 5/1996 | Ferrari et al. |
| 5,545,620 A | 8/1996 | Wahl et al. |
| 5,641,648 A | 6/1997 | Ferrari et al. |
| 5,766,897 A | 6/1998 | Braxton |
| 5,770,697 A | 6/1998 | Ferrari et al. |
| 5,792,742 A | 8/1998 | Gold et al. |
| 5,824,784 A | 10/1998 | Kinstler et al. |
| 6,018,030 A | 1/2000 | Ferrari et al. |
| 6,207,446 B1 | 3/2001 | Szostak et al. |
| 6,214,553 B1 | 4/2001 | Szostak et al. |
| 6,258,558 B1 | 7/2001 | Szostak et al. |
| 6,261,804 B1 | 7/2001 | Szostak et al. |
| 6,281,344 B1 | 8/2001 | Szostak et al. |
| 6,462,189 B1 | 10/2002 | Koide |
| 6,518,018 B1 | 2/2003 | Szostak et al. |
| 6,610,281 B2 | 8/2003 | Harris |
| 6,818,418 B1 | 11/2004 | Lipovsek et al. |
| 7,115,396 B2 | 10/2006 | Lipovsek et al. |
| 7,556,925 B2 | 7/2009 | Koide et al. |
| 7,598,352 B2 | 10/2009 | Koide |
| 7,847,062 B2 | 12/2010 | Chen et al. |
| 7,858,739 B2 | 12/2010 | Chen et al. |
| 8,067,201 B2 | 11/2011 | Morin et al. |
| 8,221,765 B2 | 7/2012 | Camphausen et al. |
| 8,258,265 B2 | 9/2012 | Koide |
| 8,263,741 B2 | 9/2012 | Koide |
| 8,278,419 B2 | 10/2012 | Jacobs et al. |
| 8,293,482 B2 | 10/2012 | Jacobs et al. |
| 8,324,362 B2 | 12/2012 | Chen et al. |
| 2002/0019517 A1 | 2/2002 | Koide |
| 2002/0044921 A1 | 4/2002 | Lee et al. |
| 2003/0170753 A1 | 9/2003 | Koide |
| 2003/0186385 A1 | 10/2003 | Koide |
| 2005/0038229 A1 | 2/2005 | Lipovsek et al. |
| 2005/0255548 A1 | 11/2005 | Lipovsek et al. |
| 2006/0210604 A1 | 9/2006 | Dadey et al. |
| 2006/0246059 A1 | 11/2006 | Lipovsek et al. |
| 2006/0270604 A1 | 11/2006 | Lipovsek et al. |
| 2007/0009478 A1 | 1/2007 | Germansen et al. |
| 2007/0082365 A1 | 4/2007 | Lipovsek et al. |
| 2008/0015339 A1 | 1/2008 | Lipovsek et al. |
| 2008/0063651 A1 | 3/2008 | Lipovsek et al. |
| 2008/0108798 A1 | 5/2008 | Lipovsek et al. |
| 2008/0139791 A1 | 6/2008 | Lipovsek et al. |
| 2008/0220049 A1 | 9/2008 | Chen et al. |
| 2009/0176654 A1 | 7/2009 | Cappuccilli et al. |
| 2010/0081792 A1 | 4/2010 | Grant et al. |
| 2010/0144601 A1 | 6/2010 | Jacobs et al. |
| 2010/0152063 A1 | 6/2010 | Cappuccilli et al. |
| 2010/0273216 A1 | 10/2010 | Morin et al. |

(Continued)

FOREIGN PATENT DOCUMENTS

| | | |
|---|---|---|
| EP | 1266025 B1 | 11/2006 |
| EP | 1137941 B1 | 8/2009 |

(Continued)

OTHER PUBLICATIONS

Ackermann, M. et al., "Anti-VEGFR2 and anti-IGF-1R-Adnectins Inhibit Ewing's Sarcoma A673-Xenograft Growth and Normalize Tumor Vascular Architecture" *Angiogenesis* 15:685-695, Springer (Aug. 23, 2012).

(Continued)

*Primary Examiner* — Yunsoo Kim

(74) *Attorney, Agent, or Firm* — Nelson Mullins Riley & Scarborough LLP; Jane E. Remillard, Esq.; Christopher L. Frank

(57) ABSTRACT

Described herein are methods for maintaining PEGylation and inhibiting dePEGylation of polypeptides, such as fibronectin-based scaffold proteins, during storage.

11 Claims, 22 Drawing Sheets

Specification includes a Sequence Listing.

(56) References Cited

U.S. PATENT DOCUMENTS

| | | |
|---|---|---|
| 2010/0298541 A1 | 11/2010 | Wu et al. |
| 2010/0322930 A1 | 12/2010 | Kolbinger et al. |
| 2011/0021746 A1 | 1/2011 | Cappuccilli et al. |
| 2011/0038866 A1 | 2/2011 | Hastewell et al. |
| 2011/0123545 A1 | 5/2011 | Marsh et al. |
| 2011/0124527 A1 | 5/2011 | Cappuccilli et al. |
| 2011/0274623 A1 | 11/2011 | Jacobs |
| 2011/0275535 A1 | 11/2011 | Loew |
| 2012/0208704 A1 | 8/2012 | Loew et al. |
| 2012/0270797 A1 | 10/2012 | Wittrup et al. |
| 2013/0079243 A1 | 3/2013 | Diem et al. |
| 2013/0079280 A1 | 3/2013 | Baca et al. |
| 2013/0096019 A1 | 4/2013 | Jacobs et al. |
| 2013/0096058 A1 | 4/2013 | Baca et al. |
| 2013/0237684 A1 | 9/2013 | Koide et al. |
| 2013/0267676 A1 | 10/2013 | Koide et al. |
| 2014/0057807 A1 | 2/2014 | Loew et al. |

FOREIGN PATENT DOCUMENTS

| | | |
|---|---|---|
| EP | 2141243 A2 | 1/2010 |
| EP | 2154535 A1 | 2/2010 |
| EP | 2385067 A1 | 11/2011 |
| EP | 2439212 A1 | 4/2012 |
| EP | 2379718 B1 | 3/2013 |
| WO | WO 94/01451 | 1/1994 |
| WO | WO 98/31700 A1 | 7/1998 |
| WO | WO 98/56915 A2 | 12/1998 |
| WO | WO 99/51773 A1 | 10/1999 |
| WO | WO 00/34784 A1 | 6/2000 |
| WO | WO 01/64942 A1 | 9/2001 |
| WO | WO 02/04523 A2 | 1/2002 |
| WO | WO 02/32925 A2 | 4/2002 |
| WO | WO 02/081497 A2 | 10/2002 |
| WO | WO 03/104418 A2 | 12/2003 |
| WO | WO 04/019861 A1 | 3/2004 |
| WO | WO 05/056764 A2 | 6/2005 |
| WO | WO 07/011166 A1 | 1/2007 |
| WO | WO 08/031098 A1 | 3/2008 |
| WO | WO 08/066752 A2 | 6/2008 |
| WO | WO 08/097497 A2 | 8/2008 |
| WO | WO 09/023184 A2 | 2/2009 |
| WO | WO 09/025806 A2 | 2/2009 |
| WO | WO 09/058379 A2 | 5/2009 |
| WO | WO 09/073115 A1 | 6/2009 |
| WO | WO 09/083804 A2 | 7/2009 |
| WO | WO 09/086116 A2 | 7/2009 |
| WO | WO 09/102421 A2 | 8/2009 |
| WO | WO 09/133208 A1 | 11/2009 |
| WO | WO 09/142773 A2 | 11/2009 |
| WO | WO 10/051274 A2 | 5/2010 |
| WO | WO 10/051310 A2 | 5/2010 |
| WO | WO 10/060095 A1 | 5/2010 |
| WO | WO 10/069913 A1 | 6/2010 |
| WO | WO 10/093627 A2 | 8/2010 |
| WO | WO 10/093771 A1 | 8/2010 |
| WO | WO 11/020033 A2 | 2/2011 |
| WO | WO 11/035202 A2 | 3/2011 |
| WO | WO 11/051333 A1 | 5/2011 |
| WO | WO 11/051466 A1 | 5/2011 |
| WO | WO 11/092233 A1 | 8/2011 |
| WO | WO 11/100700 A2 | 8/2011 |
| WO | WO 11/103105 A1 | 8/2011 |
| WO | WO 11/130324 A1 | 10/2011 |
| WO | WO 11/130354 A1 | 10/2011 |
| WO | WO 11/137319 A2 | 11/2011 |
| WO | WO 11/140086 A9 | 11/2011 |
| WO | WO 11/150133 A2 | 12/2011 |
| WO | WO 12/016245 A2 | 2/2012 |
| WO | WO 12/088006 A1 | 6/2012 |
| WO | WO 12/094653 A2 | 7/2012 |
| WO | WO 12/142515 A2 | 10/2012 |
| WO | WO 12/158678 A1 | 11/2012 |
| WO | WO 12/158739 A1 | 11/2012 |
| WO | WO 12/158818 A2 | 11/2012 |
| WO | WO 12/162418 A1 | 11/2012 |
| WO | WO 12/162426 A1 | 11/2012 |
| WO | WO 13/049275 A1 | 4/2013 |

OTHER PUBLICATIONS

Amadeo, P., et al., "Modularity and Homology: Modeling of the Titin Type I Modules and their Interfaces," *J. Mol. Biol.* 311: 283-296, Academic Press Ltd. (2001).

Baron, M., et al., "H NMR Assignment and Secondary Structure of the Cell Adhesion Type III Module of Fibronectin," *Biochemistry* 31:2068-2073, American Chemical Society, United States (1992).

Batori, V., et al., "Exploring the potential of the monobody Scaffold: Effects of Loop Elongation on the Stability of a Fibronectin Type III Domain," *Prot. Engin.* 15:1015-1020, Oxford University Press (2002).

Bazan, J.F., "Structural Design and Molecular Evolution of a Cytokine Receptor Superfamily," *Proc. Natl. Acad. Sci. USA* 87:6934-6938 (1990).

Campbell, I. D. and Spitzfaden, C., "Building proteins with fibronectin type III modules," *Structure* 2:333-337, Current Biology Ltd. (1994).

Clarke, J., et al., "Folding and Stability of a Fibronectin Type III Domain of Human Tenascin," *J. Mol. Biol.* 270:771-778, Academic Press Limited (1997).

Connelly, R.J., et al., "Mitogenic properties of a bispecific single-chain Fv-Ig fusion generated from CD2-specific mAb to distinct epitopes," *International Immunology* 10:1863-1872, Japanese Society for Immunology (1998).

Copie, V., et al., "Solution Structure and Dynamics of Linked Cell Attachment Modules of Mouse Fibronectin Containing the RGD and Synergy Regions: Comparison with the Human Fibronectin Crystal Structure," *J. Mol. Biol.* 277:663-682, Academic Press Ltd. (1998).

Cota, E., et al., "Folding of Beta-Sandwich Proteins: Three-State Transition of a Fibronectin Type III Module," *Prot. Sci.* 9:112-120, Cambridge University Press (2000).

Cota, E., et al., "Two Proteins with the Same Structure Respond Very Differently to Mutation: The Role of Plasticity in Protein Stability," *J. Mol. Biol.* 302:713-725, Academic Press (2000).

Dickinson, C. D., et al., "Crystals of the Cell-binding Module Module of Fibronectin Obtained from a Series of Recombinant Fragments Differing in length," *J. Mol. Biol.* 238:123-127, Academic Press (1994).

Dickinson, C. D., et al., "Crystal Structure of the Tenth Type III Cell Adheesion Module of Human Fibronectin," *J. Mol. Biol.* 236: 1079-1092, Academic Press (1994).

Dutta, S., et al., "High Affinity Fragment Complementation of a Fibronectin Type III Domain and its Application to Stability Enhancement," *Prot. Science* 14:2838-2848, Cold Spring Harbor Laboratory Press (2005).

Dutta, S., et al., "High-Throughput Analysis of the Protein Sequence-Stability Landscape Using a Quantitative 'Yeast Surface Two-Hybrid System' and Fragment Reconstitution," *J. Mol. Biol.* 382:721-733, Academic Press (2008).

Ely, K. R., et al., "Common molecular scaffold for two unrelated RGD molecules," *Protein Engineering* 8:823-827, Oxford University Press (1995).

Getmanova, E., et al., "Antagonists to human and mouse vascular endothelial growth factor receptor 2 generated by directed protein evolution in vitro," *Chemistry & Biology* 13:549-559, Elsevier Ltd, The Netherlands (2006).

Gilbreth, R. N., et al., "A Dominant Conformational Role for Amino Acid Diversity in Minimalist Protein-Protein Interfaces," *J. Mol. Biol.* 381:407-418, Academic Press (2008).

Gilbreth, R.N., et al., "Isoform-Specific Monobody Inhibitors of Small Ubiquitin-related Modifiers Engineered Using Structure-Guided Library Design," *Proc. Natl. Acad. Sci. USA* 108:7751-7756 (May 10, 2011).

Grebien, F., et al., "Targeting the SH2-Kinase Interface in Bcr-Abl Inhibits Leukemogenesis," *Cell* 147: 306-319, Elsevier Inc., The Netherlands (Oct. 14, 2011).

(56) References Cited

OTHER PUBLICATIONS

Hackel, B.J., et al., "Picomolar Affinity Fibronectin Domains Engineered Utilizing Loop Length Diversity, Recursive Mutagenesis, and Loop Shuffling," *J. Mol. Biol.* 381:1238-1252, Academic Press (2008).

Hackel, B.J., et al., "The Full Amino Acid Repertoire is Superior to Serine/Tyrosine for Selection of High Affinity Immunoglobulin G Binders from the Fibronectin Scaffold," *Prot. Engin., Design & Select.* 23:211-219, Oxford University Press (Jan. 12, 2010).

Hansen, C.K., "Fibronectin Type III-like Sequences and a New Domain Type in Prokaryotic Depolymerases with Insoluble Substrates," *FEBS* 305: 91-96, Elsevier Science Publishers B.V. (1992).

Huang, J., et al., "Conformation-Specific Affinity Purification of Proteins Using Engineered Binding Proteins: Application to the Estrogen Receptor," *Prot. Expr. Purificat.* 47:348-354, Elsevier, The Netherlands (2006).

Johnson et al., Monitoring manufacturing process yields, purity and stability of structural variants of PEGylated staphylokinase mutant SY161 quantitative reverse-phase chromatography, *Biomed. Chromatogr.* 17, 334-344 (2002).

Jacobs, S.A., et al., "Design of Novel Fn3 Domains with High Stability by a Consensus Sequence Approach," *Prot. Engin., Design & Selection* 25:107-117, Oxford University Press (Jan. 12, 2012).

Jacobs, S.A., et al., "FN3 Domain Engineering," in Protein Engineering Prof. Pravin Kaumaya (Ed.), ISBN: 978-953-51-0037-9, InTech, Available from http://www.intechoopen.com/books/:protein-engineering/fn3-domain engineering (Feb. 2012).

Karatan, E., et al., "Molecular Recognition Properties of FN3 Monobodies that Bind the Src SH3 Domain," *Chem. & Biol.* 11:835-844, Elsevier Ltd., The Netherlands (2004).

King, C.A., et al., "DNA vaccines with single-chain Fv fused to fragment C of tetanus toxin induce protective immunity against lymphoma and myeloma," *Nat. Med.* 4:1281-1286, Nature America, Inc., United States (1998).

Koide, A., et al., "Accelerating Phage-Display Library Selection by Reversible and Site-Specific Biotinylation," *Protein Eng., Design & Selection* 22: 685-690, Oxford University Press (2009).

Koide, A., et al., "High-Affinity Single-Domain Binding Proteins with a Binary-Code Interface," *Proc. Natl. Acad. Sci. USA* 104:6632-6637 (2007).

Koide, A., et al., "Probing Protein Conformational Changes in Living Cells by Using Designer Binding Proteins: Application to the Estrogen Receptor," *Proc. Natl. Acad. Sci. USA* 99:1253-1258 (2002).

Koide, S., et al., "Target-Binding Proteins Based on the 10th Human Fibronectin Type III Domain ([10]Fn3)," in*Methods in Enzymol.* 503: 135-156, Elsevier Inc., The Netherlands (2012).

Koide, A., et al., "Teaching an Old Scaffold New Tricks: Monobodies Constructed Using Alternative Surfaces of the Fn3 Scaffold," *J. Mol. Biol.* 415:393-405, Elsevier, The Netherlands (Dec. 16, 2012).

Koide, A., et al., "Stabilization of a Fibronectin Type III Domain by the Removal of Unfavorable Electrostatic Interactions on the Protein Surface," *Biochemistry* 40:10326-10333, American Chemical Society, United States (2001).

Koide, S., "Engineering of Recombinant Crystallization Chaperones," *Curr. Opin., Struct. Biol.* 19: 449-457, Elsevier, The Netherlands (May 2009).

Koide, S., et al., "Directed Evolution of Fibronectin Type III Domain to Novel Ligand Binding Proteins," *FASEB J.* 11:A837, Abstract No. M40, Federation for American Societies for Experimental Biology, United States (1997).

Koide, S., et al., "Directed Evolution of Fibronectin Type III Domain to Novel Ligand Binding Proteins," *FASEB J.* 11:A 1155, Abstract No. 1739, Federation for American Societies for Experimental Biology, United States (1997).

Kornblihtt, A.R., et al., "Isolation and characterizations of cDNA clones for human and bovine fibronectins," *Proc. Natl. Acad. Sci. USA* 80:3218-3222 (1983).

Leahy, D.J., et al., "2.0 a crystal structure of a four-domain segment of human fibronectin encompassing the RGD loop and synergy region," *Cell* 84:155-164, Cell Press USA, United States (1996).

Leahy, D.J., et al., "Structure of a Fibronectin Type III Domain from Tenascin Phased by MAD Analysis of the Selenomethionyl Protein," *Science* 258:987-991, American Association for the Advancement of Science, United States (1992).

Li, L., et al., "Mechanical Unfolding Intermediates Observed by Single-Molecule Force Spectroscopy in a Fibronectin Type III Module," *J. Mol. Biol.* 345:817-826, Elsevier, The Netherlands (2005).

Liao, H., et al., "mRNA Display Design of Fibronectin-Based Intrabodies That Detect and Inhibit Severe Acute Respiratory Syndrome Coronavirus Nucleocapsid Protein" *J. Biol. Chem.* 284:17512-17520, Elsevier, The Netherlands (Jun. 26, 2009).

Llpovsek, D., "Adnectins: Engineered Target-Binding Protein Therapeutics" *Protein Engineering, Design & Selection* 24: 3-9, Oxford University Press, (Nov. 10, 2010).

Llpovsek, D. et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," *J. Mol. Biol.* 368:1024-1041, Elsevier, The Netherlands (2007).

Llpovsek, D., et al., "In-vitro protein evolution by ribosome display and mRNA display," *Journal of Immunological Methods* 290:51-67, Elsevier, The Netherlands (2004).

Lltvinovich, S.V., and Ingham, K.C., "Interactions Between Type III Domains in the 110 kDa Cell-binding Fragment of Fibronectin," *J. Mol. Biol.* 248:611-626, Academic Press Ltd (1995).

Lombardo, A., et al., "Conformational flexibility and crystallization of tandemly linked type III modules of human fibronectin," *Protein Science* 5:1934-1938, Cambridge University Press (1996).

Main, A. L., et al., "The Three-Dimensional Structure of the Tenth Type III Module of Fibronectin: an Insight into RGD-Mediated Interactions," *Cell* 71:671-678, Cell Press USA, United States (1992).

Mamluk, R., et al. "Anti-Tumor Effect of CT-322 as an Adnectin Inhibitor of Vascular Endothelial Growth Factor Receptor-2," *mAbs* 2:199-208, Landes Biosceince (Mar./Apr. 2010).

Mao, Y., et al., "Fibronectin fibrillogenesis, a cell-mediated matrix assembly process," *Matrix Biology* 24:389-399, Elsevier B.V., The Netherlands (2005).

Olson, C., et al., "Design, Expression, and Stability of a Diverse Protein Library Based on the Human Fibronectin Type III Domain," *Prot. Sci.* 16:476-484, Cold Spring Harbor Laboratory Press (2007).

Parker, M.H., et al. "Antibody Mimics Based on Human Fibronectin Type Three Domain Engineered for Thermostability and High-Affinity Binding to Vascular Endothelial Growth Factor Receptor Two," *Protein Engineering, Design & Selection* 18: 435-444, Oxford University Press (2005).

Plaxco, K.W., et al., "A Comparison of the Folding Kinetics and Thermodynamics of Two Homologous Fibronectin Type III Modules," *J. Mol. Biol.* 270:763-770, Academic Press Ltd (1997).

Plaxco, K.W., et al., "Rapid refolding of a proline-rich all-beta-sheet fibronectin type III module," *Proc. Natl. Acad. Sci. USA* 93:10703-10706 (1996).

Potts, J.R. and Campbell, I.D., "Fibronectin structure and assembly," *Current Opinion in Cell Biology* 6:648-655, Current Biology Ltd. (1994).

Potts, J.R., et al., "Structure and Function of Fibronectin Modules," *Matrix Biology* 15:313-320, Gustav Fischer Verlag, Germany (1996).

Ramamurthy, V., et al., "Structures of Adnectin/Protein Complexes Reveal an Expanded Binding Footprint," *Structure* 20:259-269, Elsevier Science Ltd., The Netherlands (Feb. 8, 2012).

Richards, J., et al., "Engineered Fibronectin Type III Domain with a RGDWXE Sequence Binds with Enhanced Affinity and Specificity to Human αvβ3 Integrin," *J. Mol. Biol.* 326:1475-1488, Elsevier Science Ltd (2003).

Tolcher, A.W., et al., "Phase I and Pharmacokinetic Study of CT-322 (BMS-844203), a Targeted Adnectin Inhibitor of VEGFR-2 Based on a Domain of Human Fibronectin," *Clinical Cancer Research* 17: 363-371, American Association for the Advancement of Science, United States (Jan. 11, 2011).

(56) References Cited

OTHER PUBLICATIONS

Vuento, M. and Vaheri, A., "Purification of fibronectin from human plasma by affinity chromatography under non-denaturing conditions," *Biochem. J.* 183:331-337 (1979).

Xu, L., et al., "Directed Evolution of High-Affinity Antibody Mimics Using mRNA Display," *Chemistry & Biology* 9: 933-942, Elsevier Science Ltd., The Netherlands (2002).

Bentley et al., Poly(ethylene) Glycol Conjugates of Biopharmaceuticals, *Modern Pharmaetuicals*, 1393-1418 Weinheim, Germany (2005).

Bedu-Addo et al., Preformulation Development of Recombinant Pegylated Staphylokinase SY161 Using Statistical Design, *AAPS PharmSci*,4: 1-13, (2002).

International Search Report for WO2012/158678A1 published Nov. 22, 2012.

NCBI Entrez, GenBank Accession No. CAA26536, Kornblihtt, A.R., Apr. 21, 1993.

NCBI Entrez, GenBank Accession No. X02761, Kornblihtt, A.R., Apr. 21, 1993.

NCBI Entrez, GenBank Report, Accession No. P07589, Elsik, C.G., Dec. 19, 2008.

NCBI Entrez, GenBank Report, Accession No. AAC48614.1, MacLeod, J.N., Apr. 18, 1996.

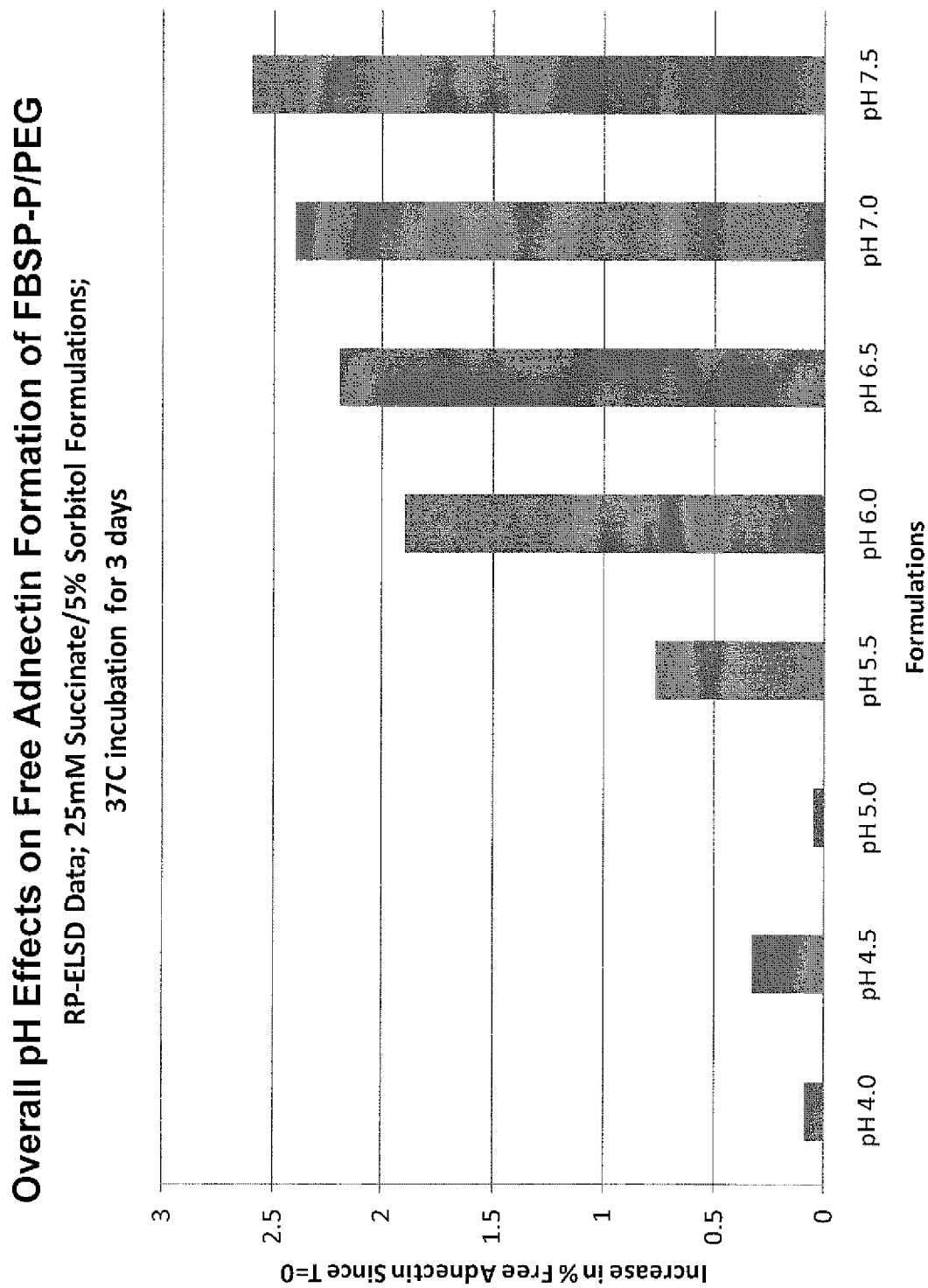

METHODS FOR MAINTAINING PEGYLATION OF POLYPEPTIDES

CROSS-REFERENCE TO RELATED APPLICATIONS

This application is a continuation of U.S. Ser. No. 14/117,458, filed on Nov. 13, 2013, which is the 371 National Stage of International Application No. PCT/US2012/037908, filed May 15, 2012, and claims priority benefit of U.S. Provisional application Ser. No. 61/487,027, filed on May 17, 2011, the contents of which are specifically incorporated by reference herein.

The instant application contains a Sequence Listing which has been submitted electronically in ASCII format and is hereby incorporated by reference in its entirety. Said ASCII copy, created on Feb. 4, 2014, is named 11722-US-PCT-_SL.txt and is 25,691 bytes in size.

BACKGROUND

PEGylation is a process by which polyethylene glycol (PEG) polymer chains are covalently conjugated to other molecules such as drugs or proteins. This chemical modification confers on the conjugate molecules many of the properties of PEG polymers, including hydrophilicity, structural flexibility, high mobility in solution, and low toxicity. With these new properties, PEGylated therapeutic agents show improved efficacy as compared to their unconjugated counterparts, due to increased serum half life, water solubility, protection from proteolytic degradation, low immunogenicity, and/or stability of the PEGylated molecules.

It is generally desirable to maintain therapeutic agents in a PEGylated state, particularly when drugs are manufactured and stored for a period of time before use. However, PEGylation is a reversible reaction and dePEGylation has been observed during formulation development, stability monitoring, and storage of some therapeutic proteins. This creates a heterogeneous mixture of PEGylated and dePEGylated molecules, which may lose efficacy, safety, and other benefits of PEGylation. Accordingly, there remains a need for maintaining PEGylation of therapeutic molecules during storage of these molecules.

SUMMARY

The present invention relates to methods for maintaining the PEGylation state of PEGylated polypeptides during periods of storage. Disclosed herein are compositions comprising a polypeptide conjugated to a PEG moiety through a maleimide linker, wherein the composition has a pH between pH 2.0 and pH 6.0. The composition may have a pH between pH 3.0 and pH 5.0. The composition may have a pH between pH 3.5 and pH 4.5. In certain embodiments, less than 5% of the maleimide linkers are cleaved over a 4, 8, 12 or more week storage period. The polypeptide may comprise a domain or region that binds specifically to a target protein, such as a tenth fibronectin type III ($^{10}$Fn3) domain having an altered amino acid sequence relative to the wild-type sequence that binds to a target molecule with a $K_D$ of less than 500 nM. The $^{10}$Fn3 domain may comprise at least one loop region that differs from a naturally occurring loop region and at least one beta strand that differs from the naturally occurring beta strand. In certain embodiments, the $^{10}$Fn3 domain does not contain a DK sequence in the C-terminal tail region. The C-terminal tail of the $^{10}$Fn3 domain may comprise a cysteine residue, to which the PEG moiety is linked. In certain embodiments, less than 1% of the maleimide linkers are cleaved over a four week storage period. The polypeptide may further comprise a second $^{10}$Fn3 domain having an altered amino acid sequence relative to the wild-type sequence that binds to a target molecule with a $K_D$ of less than 500 nM. The first and second $^{10}$Fn3 domains may bind to different targets. The first and second $^{10}$Fn3 domains may be connected by a polypeptide linker comprising from 1-30 amino acids. The polypeptide linker may be selected from the group consisting of: a glycine-serine linker, a glycine-proline linker, a proline-alanine linker and an Fn linker. The maleimide linker may form a thioether bond with a sulfhydryl group on the polypeptide. The $^{10}$Fn3 domain may comprise at least two loop regions that differ from the corresponding naturally occurring loop regions. An exemplary composition comprises a polypeptide conjugated to a PEG moiety through a maleimide linker, wherein the composition has a pH between pH 3.0 and pH 5.0 and wherein (i) the polypeptide comprises a $^{10}$Fn3 domain having an altered amino acid sequence relative to the wild-type sequence that binds to a target molecule with a $K_D$ of less than 500 nM; (ii) the $^{10}$Fn3 domain comprises at least one loop region that differs from the naturally occurring corresponding loop region and at least one beta strand that differs from the naturally occurring corresponding beta strand; (iii) the $^{10}$Fn3 domain does not contain a DK sequence in the C-terminal tail region; and the $^{10}$Fn3 domain comprises a cysteine residue, to which the PEG moiety is linked. In certain embodiments, less than 5% of the maleimide linkers are cleaved over a four week storage period.

Further disclosed herein are methods for maintaining PEGylation of polypeptides during storage by storing the polypeptides in a solution buffered to a pH between 2.0-6.0, 2.0-5.0, 2.0-4.0, 2.0-3.0, 3.0-6.0, 3.0-5.0, 3.0-4.0, 3.5-4.5, 4.0-5.0, 4.5-5.5, or 5.0-6.0. The polypeptides are conjugated to a polyethylene glycol (PEG) moiety through a maleimide linker. The maleimide linker may connect the PEG moiety to the polypeptide via a thioether bond with a sulfhydryl group on the polypeptide. In exemplary embodiments, less than 25%, 20%, 15%, 10%, 5%, 2%, 1%, 0.5%, 0.2% or 0.1% of the maleimide linkers are cleaved over a storage period of at least four weeks, eight weeks, six months, or one year.

In certain embodiments, the PEGylated polypeptides comprise a tenth fibronectin type III ($^{10}$Fn3) domain having an altered amino acid sequence relative to the wild-type sequence that binds to a target molecule with a $K_D$ of less than 500 nM. The $^{10}$Fn3 domain may have a C-terminal tail that does not contain a DK sequence, which has been found to be susceptible to cleavage in certain instances at pHs below 6.0. The $^{10}$Fn3 domain may contain a cysteine residue that serves as the site for attachment of the PEG moiety, preferably in the C-terminal tail region.

In certain embodiments, the PEGylated polypeptides are a multivalent polypeptide comprising two or more $^{10}$Fn3 domains. Each $^{10}$Fn3 domain may comprise an altered amino acid sequence relative to the wild-type sequence such that it binds to a target molecule with a $K_D$ of less than 500 nM. The first and second $^{10}$Fn3 domains bind to the same or different targets. The first and second $^{10}$Fn3 domains may be connected by a polypeptide linker comprising from 1-30 amino acids. Exemplary polypeptide linkers include, for example, a glycine-serine linker, a glycine-proline linker, a proline-alanine linker or an Fn linker.

In exemplary embodiments, the PEGylated polypeptides are stored in a formulation comprising (a) 25 mM succinate, 5% sorbitol; (b) 10 mM sodium acetate, 5% mannitol; or (c) 10 mM sodium acetate/2% mannitol, 100 mM sodium chloride.

In certain embodiments, the concentration of PEGylated polypeptides in the storage solution is from 1-10 mg/mL, 1-5 mg/mL, 0.5-2 mg/mL, or 4-6 mg/mL, or is about 1, 2, 3, 4, 5, 6, 7, 8, 9, or 10 mg/mL.

In certain embodiments, the methods involve storing the PEGylated polypeptides at a temperature from 4-30° C., 4-25° C., 4-15° C., 4-10° C., 10-30° C., or 10-25° C., or at 4, 10, 15, 20, 25 or 30° C.

In another aspect, the application provides a method for improving the stability of PEGylated polypeptides in a solution, wherein the polypeptides are conjugated to a polyethylene glycol (PEG) moiety through a maleimide linker, comprising the steps of: (a) determining the amount of PEG cleaved from the polypeptides over a fixed storage period in the solution; and (b) if PEG is cleaved from more than 5% of the polypeptides over the storage period, reformulating the PEGylated polypeptides in a storage solution buffered to a pH of between 2.0-6.0.

BRIEF DESCRIPTION OF DRAWINGS

FIG. 7 shows the increase in % free (unPEGylated) ADNECTIN™ in FBSP-P samples formulated at different pH, during 37° C. stability testing for two weeks. Free ADNECTIN™ refers to the sum of both the monomeric and dimeric form of the unPEGylated protein. Protein was formulated at 1 mg/mL in 25 mM succinate, 5% (w/v) sorbitol, at the pH indicated.

FIG. 8A shows the UV profile of a sample at 5 mg/mL protein concentration, pH 4.5. FIG. 8B shows the UV profile of a sample at 5 mg/mL, pH 5.5. FIG. 8C shows the UV profile of a sample at 5 mg/mL, pH 6.5. FIG. 8D shows the UV profile a sample at 10 mg/mL, 10 mM NaOAc, 5% mannitol, pH 6.5.

DETAILED DESCRIPTION

Overview

Figure 1:
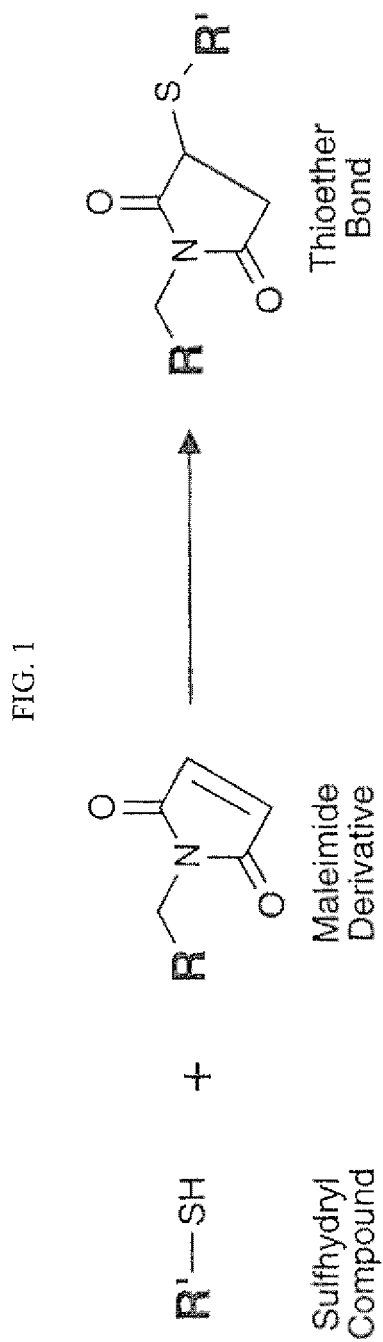
FIG. 1 illustrates the mechanism of Michael Addition, showing the ligation between a protein (R') via its sulfhydryl group and the PEG molecule (R).

The methods of the present application may be used to maintain a polyethylene glycol (PEG) moiety on PEGylated conjugates, particularly protein or peptide therapeutics, during manufacture and/or storage of the PEGylated conjugates. These methods have broad applicability to proteins and peptides that have been PEGylated to overcome issues with stability, degradation, clearance, and tolerance in subjects. The process of PEGylation links polyethylene glycol chains to candidate therapeutics to produce larger conjugates that show improved efficacy as compared to their unconjugated counterparts, due to increased serum half life, increased solubility, increased protection from proteolytic degradation, reduced immunogenicity, and/or increased stability of the PEGylated molecules.

The present application describes methods to preserve PEGylation and all of its associated benefits and methods to inhibit dePEGylation of PEGylated conjugates. Specifically, the application provides methods to inhibit cleavage of PEG moieties conjugated to polypeptides through a maleimide linker by formulating and storing the PEGylated polypeptides in a solution buffered to a pH value between pH 2.0 and pH 6.0. The methods described herein are based on the observation that certain PEGylated conjugates are subject to significant cleavage of the PEG moiety from the polypeptide resulting in regeneration of the free (unPEGylated) polypeptide and formation of protein aggregates and/or disulfide-linked polypeptide dimers. It was observed that the amount of dePEGylation depended on the pH of the formulation, and that formulations with higher pHs led to higher levels of dePEGylation. As dePEGylation has been found to be most prominent at higher pH (≥6), the present methods inhibit dePEGylation by maintaining PEGylated polypeptide conjugates at a pH below 6.0. Notably, the methods may apply to PEGylated polypeptides that are conjugated to PEG through a maleimide moiety.

Definitions

By a "polypeptide" is meant any sequence of two or more amino acids, regardless of length, post-translation modification, or function. "Polypeptide", "peptide", and "protein" are used interchangeably herein. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR®) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2. The ALIGN-2 sequence comparison computer program was authored by Genentech, Inc. has been filed with user documentation in the U.S. Copyright Office, Washington D.C., 20559, where it is registered under U.S. Copyright Registration No. TXU510087, and is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

The "half-life" of a polypeptide is the time taken for the concentration of the polypeptide to fall to half its original value. The "serum half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques for determining half-life, e.g., serum half-life, will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., *Chemical Stability of Pharmaceuticals: A Handbook for Pharmacists* (1986); Peters et al., *Pharmacokinetic Analysis: A Practical Approach* (1996); and Gibaldi, M. et al., *Pharmacokinetics*, 2nd Rev. Edition, Marcel Dekker (1982).

Half-life can be expressed using parameters such as the t1/2-alpha, t1/2-beta and the area under the curve (AUC). In the present specification, an "increase in half-life" refers to an increase in any one of these parameters, any two of these parameters, or in all three these parameters. In certain embodiments, an increase in half-life refers to an increase in the t1/2-beta, either with or without an increase in the t1/2-alpha and/or the AUC or both.

"Shelf-life" of a pharmaceutical product e.g., a PEGylated polypeptide, is the length of time the product is stored before decomposition occurs. For example, shelf-life may be defined as the time for decomposition of 0.1%, 0.5%, 1%, 5%, or 10% of the product.

A "purified" polypeptide or PEGylated polypeptide is preferably at least 85% pure, more preferably at least 95% pure, and most preferably at least 98% or 99% pure. Regardless of the exact numerical value of the purity, the polypeptide or PEGylated polypeptide is sufficiently pure for use as a pharmaceutical product.

Methods for Inhibiting DePEGylation

Given the benefits of PEGylation, it is clear that dePEGylation of PEG-protein conjugates is undesirable in many situations. DePEGylation is defined as the loss of at least one PEG moiety from a PEGylated conjugate molecule, resulting in the regeneration of the intact free polypeptide and the intact free PEG moiety. This reaction may result in decreased bioavailability, decreased blood circulation, increased immunogenicity, and decreased efficacy of a therapeutic agent, as compared to its PEGylated form. Following dePEGylation, the free polypeptides may undesirably form dimers or aggregates. For example, when the PEG molecules are attached to cysteine residues on protein molecules, dePEGylation exposes free cysteine residues that could interact with one another through intermolecular disulfide linkages to form protein dimers. Alternatively, dePEGylation may result in exposure of hydrophobic surfaces that could lead to protein aggregation.

DePEGylation may be measured using methods known in the art, such as reverse phase high performance liquid chromatography (RP-HPLC). Dual absorbance detectors may be used, for example, UV absorbance may be used for the detection of polypeptide species, while an evaporative light scattering detector (ELSD) may be used to detect the PEG moieties. In addition, liquid chromatograph-mass spectrometry (LC-MS) may be used to determine the amount of free protein molecules as well as characterize the form of the free protein as monomers, dimers, or aggregates. RP-HPLC may be used to characterize the integrity of the free PEG released from the conjugate using retention time of the released PEG as compared to the retention time for a PEG standard. For those PEGylated conjugates that were generated by maleimide chemistry, the free PEG produced by dePEGylation of the conjugate may contain the maleimide functional group.

Factors which affect PEGylation include, but are not limited to, conditions of the original PEGylation reaction, length of storage of the PEGylated molecules, storage temperature, composition of the buffers and/or solutions in which the molecules are made and/or stored, pH of the storage buffers and/or solutions, and identity of the proteins that have been conjugated to PEG.

In some embodiments of the present application, PEGylation is maintained by storing the PEGylated polypeptides in a solution buffered to a pH value between pH 2.0 and pH 6.0. In some embodiments, the PEGylated polypeptides are stored in a solution buffered to a pH value between pH 2.0-6.0, 2.0-5.0, 2.0-4.0, 2.0-3.0, 2.0-2.5, 3.0-6.0, 3.0-5.0, 3.0-4.0, 3.0-3.5, 4.0-6.0, 4.0-5.0, 4.0-4.5, 2.5-3.5, or 2.5-3.5. In some embodiments, the PEGylated polypeptides are stored in a solution buffered to a pH of 4.0, 4.5, 5.0, 5.5, or 6.0.

Suitable formulations for storing PEGylated polypeptides in accordance with the methods described herein are pharmaceutically acceptable compositions comprising a PEGylated polypeptide as described herein, wherein the composition is essentially endotoxin or pyrogen free. Formulations to be used for in vivo administration must be sterile. This is readily accomplished by filtration through sterile filtration membranes.

Therapeutic formulations comprising PEGylated polypeptides are prepared for storage by mixing the PEGylated polypeptides having the desired degree of purity with optional physiologically acceptable carriers, excipients or stabilizers (Osol, A., ed., *Remington's Pharmaceutical Sciences*, 16th Edition (1980)), in the form of aqueous solutions, lyophilized or other dried formulations. Acceptable carriers, excipients, or stabilizers are nontoxic to recipients at the dosages and concentrations employed, and include buffers such as phosphate, citrate, succinate, sodium acetate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as alanine, glycine, glutamine, asparagine, histidine, arginine, or lysine; monosaccharides, disaccharides, and other carbohydrates including glucose, mannose, or dextrans; chelating agents such as EDTA; sugars or sugar alcohols such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

Suitable solutions for storing the PEGylated polypeptides generally contain from 1-100 mM, 10-100 mM, 25-100 mM, 50-100 mM, 1-50 mM, 1-25 mM, 1-10 mM, 10-50 mM 10-25 mM, 10-20 mM, 10-15 mM of a buffering agent. In certain embodiments, the solutions for storing the PEGylated polypeptides contain 10 mM buffer or 25 mM of a buffering agent. Exemplary buffering agents include, for example, citrate, histidine, succinate or sodium acetate.

Exemplary formulations for storing PEGylated polypeptides may be selected from (a) 25 mM succinate, 5% sorbitol; (b) 10 mM sodium acetate, 5% mannitol; and (c) 10 mM sodium acetate/2% mannitol, 100 mM sodium chloride.

In certain embodiments, the concentration of PEGylated polypeptide in a formulation for storage ranges from 0.5-15 mg/mL, 0.5-5 mg/mL, 0.5-2 mg/mL, 1-10 mg/mL, 1-5 mg/mL, 1-2 mg/Ml, 3-10 mg/mL, 3-8 mg/mL, 3-6 mg/mL, 3-5 mg/mL, 4-10 mg/mL, 4-8 mg/mL, 4-6 mg/mL, 5-10 mg/mL, 5-8 mg/mL, or 5-6 mg/mL. In other embodiments, the concentration of PEGylated polypeptide in a formulation for storage may be about 1, 2, 3, 4, 5, 6, 7, 8, 9 or 10 mg/mL.

In certain embodiments, the methods described herein may be used to maintain PEGylation and/or inhibit dePEGylation of polypeptides having one, two, three, four or more PEG moieties per polypeptide molecule. In exemplary embodiments, the methods described herein are used in connection with PEGylated polypeptides having only a single PEG per polypeptide.

Formulations of PEGylated polypeptides may be suitable for administration via any desirable route. For example, the formulations may be suitable for administration intravenously as a bolus or by continuous infusion over a period of time, by intramuscular, subcutaneous, intra-articular, intra-synovial, intrathecal, oral, topical, or inhalation routes.

In certain embodiments, at least 50%, 60%, 70%, 80%, 90%, 95%, 96%, 97%, 98%, 99% or 100% of PEGylation is maintained for at least 2 weeks, 4 weeks, 3 months, 6 months, 1 year or more. PEGylation may also be maintained for over 1 year, or for as long as the activity of the PEGylated conjugate remains at therapeutically effective levels. There percentage of PEGylation maintained is determined relative to the initial level of PEGylation of the PEGylated polypeptide. For example, at least 98% of PEGylation is maintained for a two week period if less than 2% of the polypeptides have lost a PEG moiety after storage for two weeks as compared to the level of PEGylation at time zero.

The methods described herein may involve maintaining PEGylation during storage of a PEGylated polypeptide at a fixed temperature over time or during storage at variable temperatures. For example, PEGylation may be maintained during storage at 4° C., 15° C., 20° C., 25° C., 30° C., or 37° C. Alternatively, PEGylation may be maintained, for example, during storage at 4° C. for 2 weeks followed by storage at 25° C. for 1 week. In any case, the level of dePEGylation should be determined relative the initial level of PEGylation of the polypeptide.

In certain embodiments, the methods described herein may involve first determining whether a PEGylated polypeptide is subject to dePEGylation at an undesirable level when stored at pH≥6.0. For example, the methods may comprise determining the level of dePEGylation of a PEGylated polypeptide during storage at pH≥6.0. If the level of dePEGylation is greater than 1%, 2%, 5%, 10% or 15%, the PEGylated polypeptide is reformulated in a solution having a pH≤6.0. Similarly, the methods may involve monitoring the PEGylation level of a PEGylated polypeptide formulated in a solution having a pH≥6.0 for a period of time. If more than 1%, 2%, 5%, 10% or 15% of the polypeptide is dePEGylated over a period of 2 weeks, 4 weeks, 3 months or 6 months, then the polypeptide may be reformulated in a solution having a pH≤6.0.

In one embodiment, dePEGylation may be inhibited by a method comprising the steps of: (a) measuring PEGylation of the PEGylated polypeptides at an initial reference time point; (b) comparing PEGylation of the PEGylated polypeptides after an interval; (c) reducing pH of the solution to a value between pH 2.0 and pH 6.0; and (d) comparing PEGylation of the PEGylated polypeptides after an interval, wherein a decrease in dePEGylation of the PEGylated polypeptides after step (c) indicates inhibition of dePEGylation. In another embodiment, a method for inhibiting dePEGylation when storing PEGylated polypeptides may comprise: (a) storing the PEGylated polypeptides in a solution; (b) monitoring the PEGylation of the PEGylated polypeptides; and (c) lowering the pH of the solution to a value in between pH 2.0 and pH 6.0, wherein the pH is a value sufficient to inhibit dePEGylation.

PEGylated Polypeptides

The methods and formulations described herein may be applied to any PEGylated polypeptide. The methods described herein are particularly suited to maintaining PEGylation of polypeptides that are susceptible to dePEGylation when stored in solutions having a pH≥6.0. In exemplary embodiments, the PEGylated polypeptides are therapeutic proteins, such as, for example, interferon alpha, adenosine deaminase, L-asparaginase, granulocyte colony-stimulating factor and antibodies, such as, for example, anti-tumor necrosis factor alpha antibodies. A PEGylated protein may be a protein binding specifically to a target, such as an antibody or an antigen binding fragment thereof and may be any of the following: a Fab, a F(ab')2, an Fv, a single chain Fv fragment, a single domain antibody or a variant thereof (e.g., a heavy or light chain variable domain monomer or dimer, e.g., $V_H$, $V_{HH}$); a single chain Fc fragment, a diabody (dAb), a camelid antibody; one, two, or all three complementarity determining regions (CDRs) grafted onto a repertoire of VH or VL domains, or other scaffolds, an Affibody molecule (e.g., an Affibody protein Z scaffold or other molecules as described, e.g., in Lee et al., *Clin. Cancer Res.*, 14(12):3840-3849 (2008); Ahlgren et al., *Nucl. Med.*, 50:781-789 (2009)), lipocalin, ankyrin repeats, LDL receptor domain, RNA aptamer, PDZ domain, a multispecific (e.g., bivalent or bispecific) antibody or fragment thereof, a human antibody or antigen binding fragment thereof, a humanized antibody or antigen binding fragment thereof, a chimeric antibody or antigen binding fragment thereof, a camelid antibody or antigen binding fragment thereof, a shark antibody or antigen binding fragment thereof, or an in vitro generated antibody or antigen binding fragment thereof.

In an exemplary embodiment, the PEGylated polypeptide is a fibronectin based scaffold protein (FBSP) as described further below. Exemplary FBSP include, for example, monovalent FBSP that bind to, for example, PCSK9 (FBSP-P) or VEGFR2 (FBSP-V), or multivalent FBSP, including, for example, bivalent FBSP that bind to VEGFR2 and IGF-1R (FBSP-VI).

Fibronectin-Based Scaffold Proteins (FBSP)

In some embodiments, the methods disclosed herein may be used to maintain PEGylation of fibronectin based scaffold proteins. This family of proteins is capable of evolving to bind any compound of interest. These proteins generally make use of a scaffold derived from a fibronectin type III (Fn3) or Fn3-like domain and function in a manner characteristic of natural or engineered antibodies (that is, polyclonal, monoclonal, or single-chain antibodies) and, in addition, possess structural advantages. Specifically, the structure of these antibody mimics has been designed for optimal folding, stability, and solubility, even under conditions that normally lead to the loss of structure and function in antibodies. An example of fibronectin-based scaffold proteins are ADNECTINS™ (Adnexus, a wholly owned subsidiary of Bristol-Myers Squibb). Fibronectin-based scaffold proteins and ADNECTINS™ may be monovalent or multivalent.

An Fn3 domain is small, monomeric, soluble, and stable. It lacks disulfide bonds and, therefore, is stable under reducing conditions. The overall structure of Fn3 resembles the immunoglobulin fold. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face and loops BC, DE, and FG are located on the opposing face. Any or all of loops AB, BC, CD, DE, EF and FG may participate in ligand binding. There are at least 15 different modules of Fn3, and while the sequence homology between the modules is low, they all share a high similarity in tertiary structure.

The amino acid sequence of the naturally occurring human tenth fibronectin type III domain, i.e., the tenth module of human Fn3 ($^{10}$Fn3), is set forth in SEQ ID NO: 1:

(SEQ ID NO: 1)
VSDVPRDLEVVAAT<u>PTSLLI</u>SWDAPAVTVRYYRITYGE<u>TGGNSPVQEFTV</u>
PGSKST ATI<u>SGLKPGV</u>DYTITVYAVTGRGDSPASSKPISINYRT
(the AB, CD and EF loops are underlined, and the
BC. FG, and DE loops are emphasized in bold).

In SEQ ID NO: 1, the AB loop corresponds to residues 15-16, the BC loop corresponds to residues 21-30, the CD loop corresponds to residues 39-45, the DE loop corresponds to residues 51-56, the EF loop corresponds to residues 60-66, and the FG loop corresponds to residues 76-87. (Xu et al., *Chemistry & Biology*, 9:933-942 (2002)). The BC, DE and FG loops align along one face of the molecule and the AB, CD and EF loops align along the opposite face of the molecule. In SEQ ID NO: 1, beta strand A corresponds to residues 9-14, beta strand B corresponds to residues 17-20, beta strand C corresponds to residues 31-38, beta strand D corresponds to residues 46-50, beta strand E corresponds to residues 57-59, beta strand F corresponds to residues 67-75, and beta strand G corresponds to residues 88-94. The strands are connected to each other through the corresponding loop, e.g., strands A and B are connected via loop AB in the formation strand A, loop AB, strand B, etc. The first 8 amino acids of SEQ ID NO:1 (italicized above) may be deleted while still retaining binding activity of the molecule. Residues involved in forming the hydrophobic core (the "core amino acid residues") include the amino acids corresponding to the following amino acids of SEQ ID NO: 1: L8, V10, A13, L18, 120, W22, Y32, 134, Y36, F48, V50, A57, 159, L62, Y68, 170, V72, A74, 188, 190 and Y92, wherein the core amino acid residues are represented by the single letter amino acid code followed by the position at which they are located within SEQ ID NO: 1. See e.g., Dickinson et al., *J. Mol. Biol.*, 236:1079-1092 (1994).

$^{10}$Fn3 are structurally analogous to antibodies, specifically the variable region of an antibody. While $^{10}$Fn3 domains may be described as "antibody mimics" or "antibody-like proteins", they do offer a number of advantages over conventional antibodies. In particular, they exhibit better folding and thermostability properties as compared to antibodies, and they lack disulphide bonds, which are known to impede or prevent proper folding under certain conditions.

The BC, DE, and FG loops of $^{10}$Fn3 are analogous to the complementary determining regions (CDRs) from immunoglobulins. Alteration of the amino acid sequence in these loop regions changes the binding specificity of $^{10}$Fn3. $^{10}$Fn3 domains with modifications in the AB, CD and EF loops may also be made in order to produce a molecule that binds to a desired target. The protein sequences outside of the loops are analogous to the framework regions from immunoglobulins and play a role in the structural conformation of the $^{10}$Fn3. Alterations in the framework-like regions of $^{10}$Fn3 are permissible to the extent that the structural conformation is not so altered as to disrupt ligand binding. Methods for generating $^{10}$Fn3 ligand specific binders have been described in PCT Publication Nos. WO 00/034787, WO 01/64942, and WO 02/032925, disclosing high affinity TNFα binders, PCT Publication Nos. WO 2005/56764 and WO 2008/097497, disclosing high affinity VEGFR2 binders, and PCT Publication No. WO 2008/066752, disclosing high affinity IGFIR binders. Additional references discussing $^{10}$Fn3 binders (which may benefit from the methods described herein) and methods of selecting binders include PCT Publication Nos. WO 98/056915, WO 02/081497, WO 2008/031098, U.S. Publication No. 2003/186385, PCT Publication Nos. WO 2009/102421, WO 2009/142773, WO2010/060095, U.S. Pat. Nos. 6,818,418, 6,673,901, 7,115,396, PCT Publication Nos. WO 2010/0273261, WO 2011/103105, WO 2011/130354, WO 2011/140086, WO 2011/150133, WO 2010/051274, WO 2010/051310, WO 2009/086116, WO 2009/086116, WO 2010/093627, WO 2011/137319, WO 2012/016245, WO 98/056915, WO 02/081497, WO 2008/031098, U.S. Publication No. 2003/186385, PCT Publication Nos. WO 2011/130324, WO 2011/130328, WO 2009/083804, WO 2009/133208, WO 2010/093627, WO 2011/051333, WO 2011/051466, and WO 2011/092233.

As described above, amino acid residues corresponding to residues 21-30, 51-56, and 76-87 of SEQ ID NO: 1 define the BC, DE and FG loops, respectively. However, it should be understood that not every residue within the loop region needs to be modified in order to achieve a $^{10}$Fn3 binder having strong affinity for a desired target. For example, in many cases, only residues corresponding to amino acids 23-30 of the BC loop and 52-55 of the DE loop are modified and result in high affinity $^{10}$Fn3 binders. Accordingly, in certain embodiments, the BC loop may be defined by amino acids corresponding to residues 23-30 of SEQ ID NO: 1, and the DE loop may be defined by amino acids corresponding to residues 52-55 of SEQ ID NO: 1. Additionally, insertions and deletions in the loop regions may also be made while still producing high affinity $^{10}$Fn3 binders.

Accordingly, in some embodiments, one or more loops selected from BC, DE, and FG may be extended or shortened in length relative to the corresponding loop in wild-type human $^{10}$Fn3. In some embodiments, the length of the loop may be extended by from 2-25 amino acids. In some embodiments, the length of the loop may be decreased by 1-11 amino acids. In particular, the FG loop of $^{10}$Fn3 is 12 residues long, whereas the corresponding loop in antibody heavy chains ranges from 4-28 residues. To optimize antigen binding, therefore, the length of the FG loop of $^{10}$Fn3 may be altered in length as well as in sequence to cover the CDR3 range of 4-28 residues to obtain the greatest possible flexibility and affinity in antigen binding. In some embodiments, the integrin-binding motif "arginine-glycine-aspartic acid" (RGD), located at residues 79-81 of SEQ ID NO: 1, may be modified in order to disrupt integrin binding. For example, the RGD sequence may be replaced with SGE.

The non-ligand binding sequences of $^{10}$Fn3, i.e., the "$^{10}$Fn3 scaffold", may be altered provided that the $^{10}$Fn3 retains ligand binding function and/or structural stability. In some embodiments, one or more of Asp 7, Glu 9, and Asp 23 are replaced by another amino acid, such as, for example, a non-negatively charged amino acid residue (e.g., Asn, Lys, etc.). These mutations have been reported to have the effect of promoting greater stability of the mutant $^{10}$Fn3 at neutral pH as compared to the wild-type form (See, PCT Publication No. WO 02/04523). A variety of additional alterations in the $^{10}$Fn3 scaffold that are either beneficial or neutral have been disclosed. See, for example, Baton et al., *Protein Eng.*, 15(12):1015-1020 (2002); Koide et al., *Biochemistry*, 40(34):10326-10333 (2001).

Residues involved in forming the hydrophobic core (the "core amino acid residues") in SEQ ID NO: 1 include the amino acids corresponding to the following amino acids of SEQ ID NO: 1: L8, V10, A13, L18, 120, W22, Y32, 134, Y36, F48, V50, A57, 159, L62, Y68, 170, V72, A74, 188, 190 and Y92, wherein the core amino acid residues are represented by the single letter amino acid code followed by the position at which they are located within SEQ ID NO: 1. See e.g., Dickinson et al., *J. Mol. Biol.*, 236:1079-1092 (1994). In some embodiments, the hydrophobic core amino acids are not modified relative to the wild-type sequence. In other embodiments, the following hydrophobic amino acids may be mutated: W22 and/or L62.

The $^{10}$Fn3 scaffold may be modified by one or more conservative substitutions. As many as 5%, 10%, 20% or even 30% or more of the amino acids in the $^{10}$Fn3 scaffold may be altered by a conservative substitution without substantially altering the affinity of the $^{10}$Fn3 for a ligand. In certain embodiments, the scaffold may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In certain embodiments, the substitutions in the scaffold do not include substitutions of the hydrophobic core amino acid residues. Preferably, the scaffold modification reduces the binding affinity of the $^{10}$Fn3 binder for a ligand by less than 100-fold, 50-fold, 25-fold, 10-fold, 5-fold, or 2-fold. It may be that such changes will alter the immunogenicity of the $^{10}$Fn3 in vivo, and where the immunogenicity is decreased, such changes will be desirable. As used herein, "conservative substitutions" refers to replacement of one amino acid with another amino acid that is physically or functionally similar to the amino acid being replaced. That is, a conservative substitution and its reference residue have similar size, shape, electric charge, chemical properties including the ability to form covalent or hydrogen bonds, or the like. Preferred conservative substitutions are those fulfilling the criteria defined for an accepted point mutation in Dayhoff et al., *Atlas of Protein Sequence and Structure*, 5:345-352 (1978 & Supp.). Examples of conservative substitutions are substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

In some embodiments, a fibronectin based scaffold protein comprises a $^{10}$Fn3 domain having at least 40%, 50%, 55%, 60%, 65%, 70%, 75%, 80%, 85%, or 90% identity to the human $^{10}$Fn3 domain having the amino acid sequence of SEQ ID NO: 1. Much of the variability will generally occur in one or more of the loops. Each of the beta or beta-like strands of a $^{10}$Fn3 domain in a fibronectin based scaffold protein may comprise, consist essentially of, or consist of an amino acid sequence that is at least 80%, 85%, 90%, 95% or 100% identical to the sequence of a corresponding beta or beta-like strand of SEQ ID NO: 1, provided that such variation does not disrupt the stability of the polypeptide in physiological conditions. In exemplary embodiments, the $^{10}$Fn3 domain binds to a desired target with a $K_D$ of less than 500 nM, 100 nM, 10 nM, 1 nM, 500 pM, 100 pM or less. In exemplary embodiments, the fibronectin based scaffold protein binds specifically to a target that is not bound by a wild-type $^{10}$Fn3 domain, particularly the wild-type human $^{10}$Fn3 domain.

In some embodiments, the fibronectin based scaffold protein comprises a $^{10}$Fn3 domain having an amino acid sequence at least 80, 85, 90, 95, 98, or 100% identical to the non-loop regions of SEQ ID NO: 1, wherein at least one loop selected from BC, DE, and FG is altered. In some embodiments, the altered BC loop has up to 10 amino acid substitutions, up to 4 amino acid deletions, up to 10 amino acid insertions, or a combination thereof. In some embodiments, the altered DE loop has up to 6 amino acid substitutions, up to 4 amino acid deletions, up to 13 amino acid insertions, or a combination thereof. In some embodiments, the FG loop has up to 12 amino acid substitutions, up to 11 amino acid deletions, up to 25 amino acid insertions, or a combination thereof.

In some embodiments, the disclosure provides polypeptides comprising a $^{10}$Fn3 domain, wherein the $^{10}$Fn3 domain comprises a loop, AB; a loop, BC; a loop, CD; a loop, DE; a loop, EF; and a loop, FG; and has at least one loop selected from loop BC, DE, and FG with an altered amino acid sequence relative to the sequence of the corresponding loop of the human $^{10}$Fn3 domain. In some embodiments, the BC and FG loops are altered. In some embodiments, the BC, DE, and FG loops are altered, i.e., the $^{10}$Fn3 domain comprises non-naturally occurring loops. By "altered" is meant one or more amino acid sequence alterations relative to a template sequence (i.e., the corresponding human fibronectin domain) and includes amino acid additions, deletions, and substitutions. Altering an amino acid sequence may be accomplished through intentional, blind, or spontaneous sequence variation, generally of a nucleic acid coding sequence, and may occur by any technique, for example, PCR, error-prone PCR, or chemical DNA synthesis.

In certain embodiments, antibody-like proteins based on the $^{10}$Fn3 scaffold can be defined generally by the following core amino acid sequence:

```
                                            (SEQ ID NO: 2)
EVVAAT(X)ₐSLLI(X)ₓYYRITGE(X)ᵦQEFTV(X)ᵧATI(X)ᵢ
DYTITVYAV(X)ᵤISINYRT
```

In SEQ ID NO: 2, the AB loop is represented by $X_a$, the CD loop is represented by $X_b$, the EF loop is represented by $X_c$, the BC loop is represented by $X_x$, the DE loop is represented by $X_y$, and the FG loop is represented by $X_z$. X represents any amino acid and the subscript following the X represents an integer of the number of amino acids. In particular, a may be anywhere from 1-15, 2-15, 1-10, 2-10, 1-8, 2-8, 1-5, 2-5, 1-4, 2-4, 1-3, 2-3, or 1-2 amino acids; and b, c, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, a is 2 amino acids, b is 7 amino acids, c is 7 amino acids, x is 9 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the hydrophobic core amino acid residues are fixed and any substitutions, conservative substitutions, deletions or additions occur at residues other than the core amino acid residues. In exemplary embodiments, the BC, DE, and FG loops as represented by $(X)_x$, $(X)_y$, and $(X)_z$, respectively, are replaced with polypeptides comprising BC, DE and FG loop sequences that bind to specific targets.

In certain embodiments, Antibody-like proteins based on the $^{10}$Fn3 scaffold can be defined generally by the sequence:

(SEQ ID NO: 3)
EVVAATPTSLLI(X)$_x$YYRITYGETGGNSPVQEFTV(X)$_y$ATISGLKPGV
DYTITVYAV(X)$_z$ISINYRT

In SEQ ID NO: 3, the BC loop is represented by X$_x$, the DE loop is represented by X$_y$, and the FG loop is represented by X$_z$. X represents any amino acid and the subscript following the X represents an integer of the number of amino acids. In particular, x, y and z may each independently be anywhere from 2-20, 2-15, 2-10, 2-8, 5-20, 5-15, 5-10, 5-8, 6-20, 6-15, 6-10, 6-8, 2-7, 5-7, or 6-7 amino acids. In preferred embodiments, x is 9 amino acids, y is 6 amino acids, and z is 12 amino acids. The sequences of the beta strands may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NO: 1. In an exemplary embodiment, the sequences of the beta strands may have anywhere from 0 to 10, from 0 to 8, from 0 to 6, from 0 to 5, from 0 to 4, from 0 to 3, from 0 to 2, or from 0 to 1 conservative substitutions across all 7 scaffold regions relative to the corresponding amino acids shown in SEQ ID NO: 1. In certain embodiments, the core amino acid residues are fixed and any substitutions, conservative substitutions, deletions or additions occur at residues other than the core amino acid residues. In exemplary embodiments, the BC, DE, and FG loops as represented by (X)$_x$, (X)$_y$, and (X)$_z$, respectively, are replaced with polypeptides comprising BC, DE and FG loop sequences that bind to specific targets.

A $^{10}$Fn3 domain as described herein may optionally contain a modified N- and/or C-terminal sequence. For example, with reference to SEQ ID NO: 2 or 3, the $^{10}$Fn3 domain may comprise an N-terminal extension and/or a C-terminal tail as described further below.

In certain embodiments, the $^{10}$Fn3 domain as shown in SEQ ID NO: 2 or 3 may optionally comprise an N-terminal extension of from 1-20, 1-15, 1-10, 1-8, 1-5, 1-4, 1-3, 1-2, or 1 amino acids in length. Exemplary N-terminal extensions include (represented by the single letter amino acid code) M, MG, G, MGVSDVPRDL (SEQ ID NO: 17), VSDVPRDL (SEQ ID NO: 18), and GVSDVPRDL (SEQ ID NO: 19), or N-terminal truncations of any one of SEQ ID NOs: 17, 18 or 19. Other suitable N-terminal extensions include, for example, X$_n$SDVPRDL (SEQ ID NO: 20), X$_n$DVPRDL (SEQ ID NO: 21), X$_n$VPRDL (SEQ ID NO: 22), X$_n$PRDL (SEQ ID NO: 23), X$_n$RDL (SEQ ID NO: 24), X$_n$DL (SEQ ID NO: 25), or X$_n$L (SEQ ID NO: 51), wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus.

In certain embodiments, the $^{10}$Fn3 domain as shown in SEQ ID NO: 2 or 3 may optionally comprise a C-terminal tail of from 1-20, 1-15, 1-10, 1-8, 1-5, or 1-4 amino acids in length. Specific examples of tail sequences include, for example, polypeptides comprising, consisting essentially of, or consisting of, EIEK (SEQ ID NO: 5), EGSGC (SEQ ID NO: 10), EIEKPCQ (SEQ ID NO: 11), EIEKPSQ (SEQ ID NO: 26), EIEKP (SEQ ID NO: 27), EIEKPS (SEQ ID NO: 28), EIEKPC (SEQ ID NO: 12), EIDKPSQ (SEQ ID NO: 14), or EIDKPSQLE (SEQ ID NO: 16). In certain embodiments, the $^{10}$Fn3 domain comprises a C-terminal tail comprising a sequence X(ED)$_n$(SEQ ID NO: 52), wherein n is an integer from 2-10, 2-8, 2-5, 3-10, 3-8, 3-7, 3-5, 4-7, or wherein n is 2, 3, 4, 5, 6, 7, 8, 9 or 10, and X is optional, and when present is an E, I or EI. Such ED repeat tails may enhance solubility and/or reduce aggregation of the $^{10}$Fn3 domain. In exemplary embodiments, the C-terminal tail comprises, consists essentially of, or consists of the amino acid sequence of SEQ ID NO: 11. In preferred embodiments, the C-terminal sequences lack DK sequences. In exemplary embodiments, the C-terminal tail comprises a residue that facilitates modification by PEG, i.e., a lysine or cysteine residue. In preferred embodiments, the C-terminal tail lacks a DK sequence and comprises a cysteine residue.

In certain embodiments, the fibronectin based scaffold proteins comprise a $^{10}$Fn3 domain having both an N-terminal extension and a C-terminal tail.

Multivalent Fibronectin Based Scaffold Proteins

In certain embodiments, the fibronectin based scaffold protein is a multivalent protein that comprises two or more $^{10}$Fn3 domains as described herein. For example, a multivalent fibronectin based scaffold protein may comprise 2, 3 or more $^{10}$Fn3 domains that are covalently associated. In exemplary embodiments, the fibronectin based scaffold protein is a bispecific or dimeric protein comprising two $^{10}$Fn3 domains. In certain embodiments, a multivalent fibronectin based protein scaffold comprises a first $^{10}$Fn3 domain that binds to a first target molecule and a second $^{10}$Fn3 domain that binds to a second target molecule. The first and second target molecules may be the same or different target molecules. When the first and second target molecules are the same, the $^{10}$Fn3 domains, i.e., the binding loops, may be the same or different. Furthermore, when the first and second $^{10}$Fn3 domains bind to the same target, they may bind to the same or different epitopes on the target.

In exemplary embodiments, each $^{10}$Fn3 domain of a multivalent fibronectin based protein scaffold binds to a desired target with a $K_D$ of less than 500 nM, 100 nM, 10 nM, 1 nM, 500 pM, 100 pM or less. In exemplary embodiments, each $^{10}$Fn3 domain of a multivalent fibronectin based protein scaffold binds specifically to a target that is not bound by a wild-type $^{10}$Fn3 domain, particularly the wild-type human $^{10}$Fn3 domain.

The $^{10}$Fn3 domains in a multivalent fibronectin based scaffold protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. The application provides that suitable linkers that meet these requirements comprise glycine-serine based linkers, glycine-proline based linkers, proline-alanine based linkers as well as the linker SEQ ID NO: 31. The Examples described in WO 2009/142773 demonstrate that Fn3 domains joined via these linkers retain their target binding function. In some embodiments, the linker is a glycine-serine based linker. These linkers comprise glycine and serine residues and may be between 8 and 50, 10 and 30, and 10 and 20 amino acids in length. Examples of such linkers include SEQ ID NOs: 32-36. In some embodiments, the linker is a glycine-proline based linker. These linkers comprise glycine and proline residues and may be between 3 and 30, 10 and 30, and 3 and 20 amino acids in length. Examples of such linkers include SEQ ID NOs: 37, 38 and 39. In some embodiments, the linker is a proline-alanine based linker. These linkers comprise proline and alanine residues and may be between 3 and 30, 10 and 30, 3 and 20 and 6 and 18 amino acids in length. Examples of such linkers include SEQ ID NOs: 40, 41 and 42. It is contemplated, that the optimal linker length and amino acid composition may be determined by routine experimentation based on the teachings provided herein. In exemplary embodiments, the linker does not contain any DK sequences. In certain embodiments, the linker may be a C-terminal tail polypeptide as described herein, an N-terminal extension polypeptide as described herein, a linker polypeptide as described herein, or any combination thereof.

In the case of multivalent fibronectin based scaffold proteins, preferably none of the $^{10}$Fn3 domains comprise a C-terminal tail containing a DK sequence. In exemplary embodiments, a multivalent fibronectin based scaffold protein comprises two or more $^{10}$Fn3 domains, wherein each domain comprises a C-terminal tail that does not contain a DK sequence. In certain embodiments, a multivalent fibronectin based scaffold protein comprises two or more $^{10}$Fn3 domains, wherein each domain comprises a C-terminal tail that does not contain a DK sequence and at least one of the domains comprises a residue suitable for addition of a PEG moiety, such as a lysine or cysteine residue.

PEGylation

PEG is a well-known, water soluble polymer that may be obtained commercially or prepared by ring-opening polymerization of ethylene glycol according to methods well known in the art (Sandler et al., *Polymer Synthesis*, Vol. 3, pp. 138-161, Academic Press, N.Y.). The term "PEG" is used broadly to encompass any polyethylene glycol molecule, without regard to size or to modification at an end of the PEG, and can be represented by the formula:

X—O(CH$_2$CH$_2$O)$_{n-1}$CH$_2$CH$_2$OH (1), where n is 20 to 2300 and X is H or a terminal modification, e.g., a C$_{1-4}$ alkyl. In one embodiment, the PEG of the invention terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, European Published Application No. 473084A and U.S. Pat. No. 5,932,462. One form of PEGs includes two PEG side-chains (PEG2) linked via the primary amino groups of a lysine (Monfardini, C. et al., *Bioconjugate Chem.*, 6:62-69 (1995)).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al., *J. Biol. Chem.*, 252:3571 (1977) and *J. Biol. Chem.*, 252:3582 (1977), Zalipsky et al. and Harris et al., in: *Poly(ethylene glycol) Chemistry: Biotechnical and Biomedical Applications*, Chapters 21 and 22, Harris, J. M., ed., Plenum Press, N.Y. (1992)). It is noted that a polypeptide containing a PEG molecule is also known as a conjugated or PEGylated protein, whereas the protein lacking an attached PEG molecule can be referred to as unconjugated or free.

The size of PEG utilized will depend on several factors including the intended use of the polypeptide. Larger PEGs are preferred to increase half life in the body, blood, non-blood extracellular fluids or tissues. For in vivo cellular activity, PEGs of the range of about 10 to 60 kDa are preferred, as well as PEGs less than about 100 kDa and more preferably less than about 60 kDa, though sizes greater than about 100 kDa can be used as well. For in vivo imaging applications, smaller PEGs, generally less than about 20 kDa, may be used that do not increase half life as much as larger PEGs so as to permit quicker distribution and less half life. A variety of molecular mass forms of PEG can be selected, e.g., from about 1,000 Daltons (Da) to 100,000 Da (n is 20 to 2300), for conjugating to polypeptides of the invention. The number of repeating units "n" in the PEG is approximated for the molecular mass described in Daltons. It is preferred that the combined molecular mass of PEG on an activated linker is suitable for pharmaceutical use. Thus, in one embodiment, the molecular mass of the PEG molecules does not exceed 100,000 Da. For example, if three PEG molecules are attached to a linker, where each PEG molecule has the same molecular mass of 12,000 Da (each n is about 270), then the total molecular mass of PEG on the linker is about 36,000 Da (total n is about 820). The molecular masses of the PEG attached to the linker can also be different, e.g., of three molecules on a linker two PEG molecules can be 5,000 Da each (each n is about 110) and one PEG molecule can be 12,000 Da (n is about 270). In some embodiments, one PEG moiety is conjugated to the polypeptide. In some embodiments, the PEG moiety is about 30, 40, 50, 60, 70, 80, or 90 KDa.

In some embodiments, PEGylated polypeptides contain one, two or more PEG moieties. In one embodiment, the PEG moiety(ies) are bound to an amino acid residue which is on the surface of the protein and/or away from the surface that contacts the target ligand. In one embodiment, the combined or total molecular mass of PEG in a PEGylated polypeptide is from about 3,000 Da to 60,000 Da, from about 10,000 Da to 36,000 Da, or from about 35,000 Da to 45,000 Da, or about 40,000 Da. In a one embodiment, the PEG in a PEGylated polypeptide is a substantially linear, straight-chain PEG.

One skilled in the art can select a suitable molecular mass for PEG, e.g., based on how the pegylated polypeptide will be used therapeutically, the desired dosage, circulation time, resistance to proteolysis, immunogenicity, and other considerations. For a discussion of PEG and its use to enhance the properties of proteins, see Katre, N. V., *Advanced Drug Delivery Reviews*, 10:91-114 (1993).

In some embodiments, a polypeptide is covalently linked to one poly(ethylene glycol) group of the formula: —CO—(CH$_2$)$_x$—(OCH$_2$CH$_2$)$_m$—OR, with the —CO (i.e., carbonyl) of the poly(ethylene glycol) group forming an amide bond with one of the amino groups of the polypeptide; R being lower alkyl; x being 2 or 3; m being from about 450 to about 950; and n and m being chosen so that the molecular weight of the conjugate minus the polypeptide is from about 10 to 40 kDa. In one embodiment, a polypeptide's ε-amino group of a lysine is the available (free) amino group.

In one specific embodiment, carbonate esters of PEG are used to form the PEG-polypeptide conjugates. N,N'-disuccinimidylcarbonate (DSC) may be used in the reaction with PEG to form active mixed PEG-succinimidyl carbonate that may be subsequently reacted with a nucleophilic group of a linker or an amino group of a polypeptide (see U.S. Pat. Nos. 5,281,698 and 5,932,462). In a similar type of reaction, 1,1'-(dibenzotriazolyl)carbonate and di-(2-pyridyl)carbonate may be reacted with PEG to form PEG-benzotriazolyl and PEG-pyridyl mixed carbonate (U.S. Pat. No. 5,382, 657), respectively.

PEGylation of a polypeptide can be performed according to the methods of the state of the art, for example by reaction of the polypeptide with electrophilically active PEGs (supplier: Shearwater Corp., USA, www.shearwatercorp.com). Preferred PEG reagents of the present invention are, e.g., N-hydroxysuccinimidyl propionates (PEG-SPA), butanoates (PEG-SBA), PEG-succinimidyl propionate or branched N-hydroxysuccinimides such as mPEG2-NHS (Monfardini, C., et al., *Bioconjugate Chem.*, 6:62-69 (1995)). Such methods may used to pegylate at an ε-amino group of a polypeptide lysine or the N-terminal amino group of the polypeptide.

In another embodiment, PEG molecules may be coupled to sulfhydryl groups on a polypeptide (Sartore, L. et al., *Appl. Biochem. Biotechnol.*, 27:45 (1991); Morpurgo et al., *Bioconjugate Chem.*, 7:363-368 (1996); Goodson et al., *Bio/Technology*, 8:343 (1990); U.S. Pat. No. 5,766,897). U.S. Pat. Nos. 6,610,281 and 5,766,897 describe exemplary reactive PEG species that may be coupled to sulfhydryl groups.

In some embodiments, the pegylated polypeptide is produced by site-directed PEGylation, particularly by conjugation of PEG to a cysteine moiety at the N- or C-terminus. In some embodiments, the polypeptide is an Fn3 domain covalently bound to a PEG moiety, wherein at least one of the loops of said Fn3 domain participates in binding to a target. The PEG moiety may be attached to the Fn3 polypeptide by site directed PEGylation, such as by attachment to a Cys residue, where the Cys residue may be positioned at the N-terminus of the Fn3 polypeptide or between the N-terminus and the most N-terminal beta or beta-like strand or at the C-terminus of the Fn3 polypeptide or between the C-terminus and the most C-terminal beta or beta-like strand. A Cys residue may be situated at other positions as well, particularly any of the loops that do not participate in target binding. A PEG moiety may also be attached by other chemistry, including by conjugation to amines.

In some embodiments where PEG molecules are conjugated to cysteine residues on a polypeptide, the cysteine residues are native to the polypeptide, whereas in other embodiments, one or more cysteine residues are engineered into the polypeptide. Mutations may be introduced into a polypeptide coding sequence to generate cysteine residues. This might be achieved, for example, by mutating one or more amino acid residues to cysteine. Preferred amino acids for mutating to a cysteine residue include serine, threonine, alanine and other hydrophilic residues. Preferably, the residue to be mutated to cysteine is a surface-exposed residue. Algorithms are well-known in the art for predicting surface accessibility of residues based on primary sequence or a protein. Alternatively, surface residues may be predicted by comparing the amino acid sequences of polypeptides, given that the crystal structure of the framework based on which polypeptides are designed and evolved has been solved (see Himanen et al., *Nature*, 414(6866):933-938 (Dec. 20-27, 2001)) and thus the surface-exposed residues identified. In one embodiment, cysteine residues are introduced into polypeptides at or near the N- and/or C-terminus, or within loop regions. PEGylation of cysteine residues may be carried out using, for example, PEG-maleimide, PEG-vinylsulfone, PEG-iodoacetamide, or PEG-orthopyridyl disulfide. In exemplary embodiments, polypeptides are PEGylated on a cysteine residue using a maleimide linker.

In some embodiments, the pegylated polypeptide comprises a PEG molecule covalently attached to the alpha amino group of the N-terminal amino acid. Site specific N-terminal reductive amination is described in Pepinsky et al., *J. Pharmacol. Exp. Ther.*, 297:1059 (2001), and U.S. Pat. No. 5,824,784. The use of a PEG-aldehyde for the reductive amination of a protein utilizing other available nucleophilic amino groups is described in U.S. Pat. No. 4,002,531, in Wieder et al., *J. Biol. Chem.*, 254:12579 (1979), and in Chamow et al., *Bioconjugate Chem.*, 5:133 (1994).

In another embodiment, pegylated polypeptide comprises one or more PEG molecules covalently attached to a linker, which in turn is attached to the alpha amino group of the amino acid residue at the N-terminus of the polypeptide. Such an approach is disclosed in U.S. Publication No. 2002/0044921 and PCT Publication No. WO 94/01451.

In one embodiment, a polypeptide is PEGylated at the C-terminus. In a specific embodiment, a protein is pegylated at the C-terminus by the introduction of C-terminal azidomethionine and the subsequent conjugation of a methyl-PEG-triarylphosphine compound via the Staudinger reaction. This C-terminal conjugation method is described in Cazalis et al., "C-Terminal Site-Specific PEGylation of a Truncated Thrombomodulin Mutant with Retention of Full Bioactivity", *Bioconjugate Chem.*, 15(5):1005-1009 (2004).

In exemplary embodiments, a fibronectin based scaffold protein is pegylated in a C-terminal tail region as described further herein. Exemplary C-terminal tails include, for example, a polypeptide having any one of SEQ ID NOs: 10, 11, or 12.

In some embodiments, a branched PEG moiety may be conjugated to a protein via a lone cysteine residue on the protein. The chemistry of this conjugation may be, for example, highly selective maleimide chemistry in which free electrons on the sulfhydryl group on the protein attach to the maleimide group on the PEG via Michael Addition (FIG. 1, where the protein is represented by R' and PEG molecule is represented by R). Specifically, the maleimide moiety forms a thioether bond with a sulfhydryl group on the protein. The Michael Addition reaction may be performed at a pH between pH 5.0 and pH 5.5 inclusive, or between pH 6.0 and 8.0 inclusive.

Conventional separation and purification techniques known in the art can be used to purify PEGylated polypeptides, such as size exclusion (e.g., gel filtration) and ion exchange chromatography. Products may also be separated using SDS-PAGE. Products that may be separated include mono-, di-, tri-, poly- and un-pegylated polypeptides, as well as free PEG. The percentage of mono-PEG conjugates can be controlled by pooling broader fractions around the elution peak to increase the percentage of mono-PEG in the composition. About ninety percent mono-PEG conjugates represents a good balance of yield and activity. Compositions in which, for example, at least ninety-two percent or at least ninety-six percent of the conjugates are mono-PEG species may be desired.

In certain embodiments, the pegylated polypeptides will preferably retain at least about 25%, 50%, 60%, 70%, 80%, 85%, 90%, 95% or 100% of the biological activity associated with the unmodified protein. In one embodiment, biological activity refers to its ability to bind to its target, as assessed by $K_D$, $k_{on}$ or $k_{off}$.

The serum clearance rate of PEG-modified polypeptides may be decreased by about 10%, 20%, 30%, 40%, 50%, 60%, 70%, 80%, or even 90%, relative to the clearance rate of the unmodified polypeptide. The PEG-modified polypeptide may have a half-life ($t_{1/2}$) which is enhanced relative to the half-life of the unmodified protein. The half-life of the PEG-polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified polypeptide. In some embodiments, the protein half-life is determined in vitro, such as in a buffered saline solution or in serum. In other embodiments, the protein half-life is an in vivo half life, such as the half-life of the protein in the serum or other bodily fluid of an animal.

In certain embodiments, a PEGylated polypeptide has a shelf-life of at least 6 months, 1 year, 2 years, 3 years, 4 years, 5 years or more when formulated at a pH between pH 2.0 and pH 6.0 (e.g., a pH between pH 3.0 and 5.0).

EXAMPLES

The invention now being generally described will be more readily understood by reference to the following examples which are included merely for purposes of illustration of certain aspects and embodiments of the present invention, and are not intended to limit the invention in any way.

Example 1

Effects of pH on DePEGylation of FBSP-P

Figure 2A:
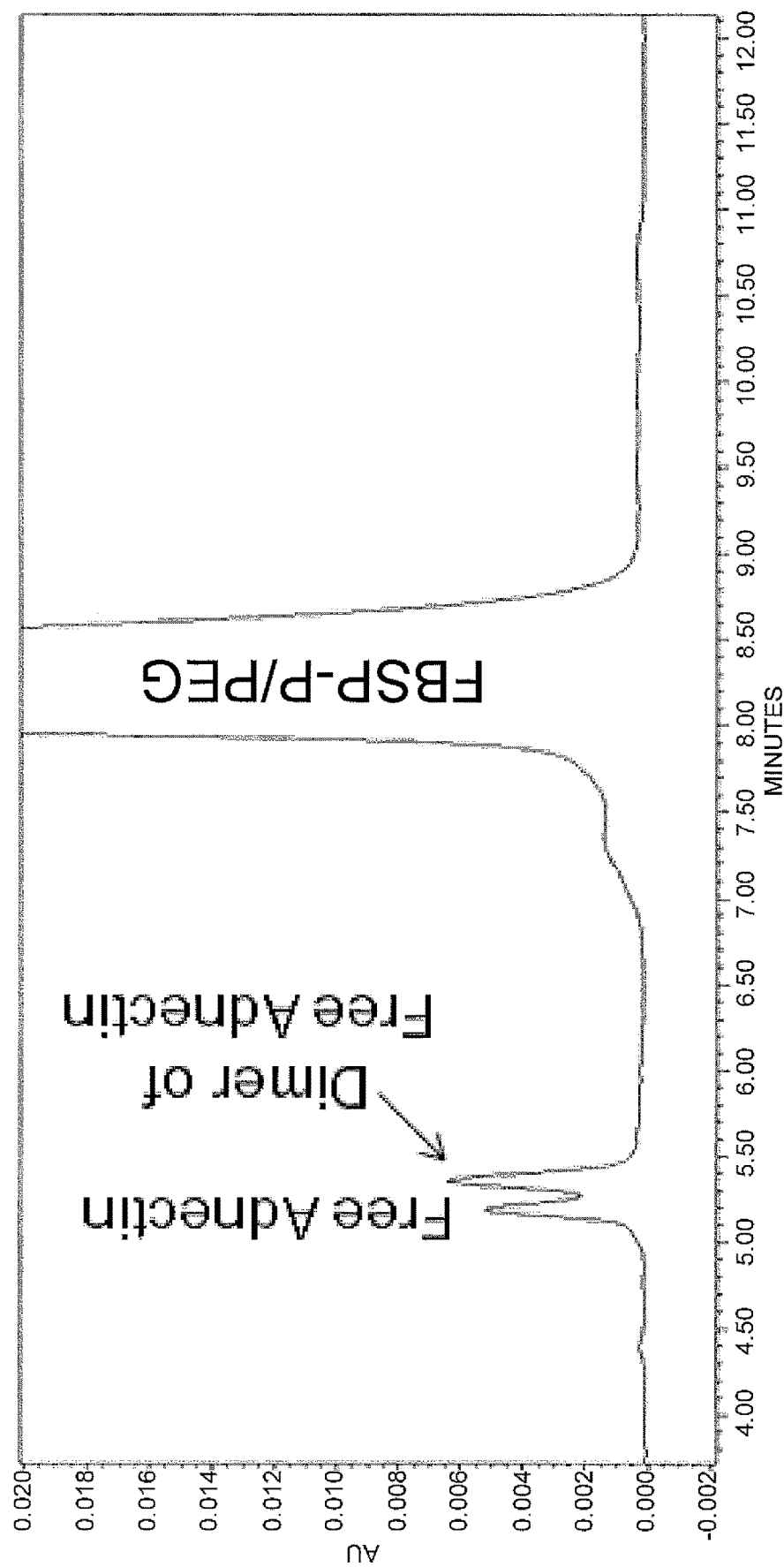
FIG. 2A-B shows the RP-HPLC profile of a FBSP-P stability sample (10 mg/mL, formulated in 10 mM succinate, 5% (w/v) sorbitol, 1.2% (w/v) alanine, pH 6.0; incubated at 25° C. for four weeks). A: UV trace at 280 nm depicting the detection of free (unPEGylated) FBSP-P ADNECTIN™. B: ELSD trace showing the detection of free intact PEG.
Figure 2B:
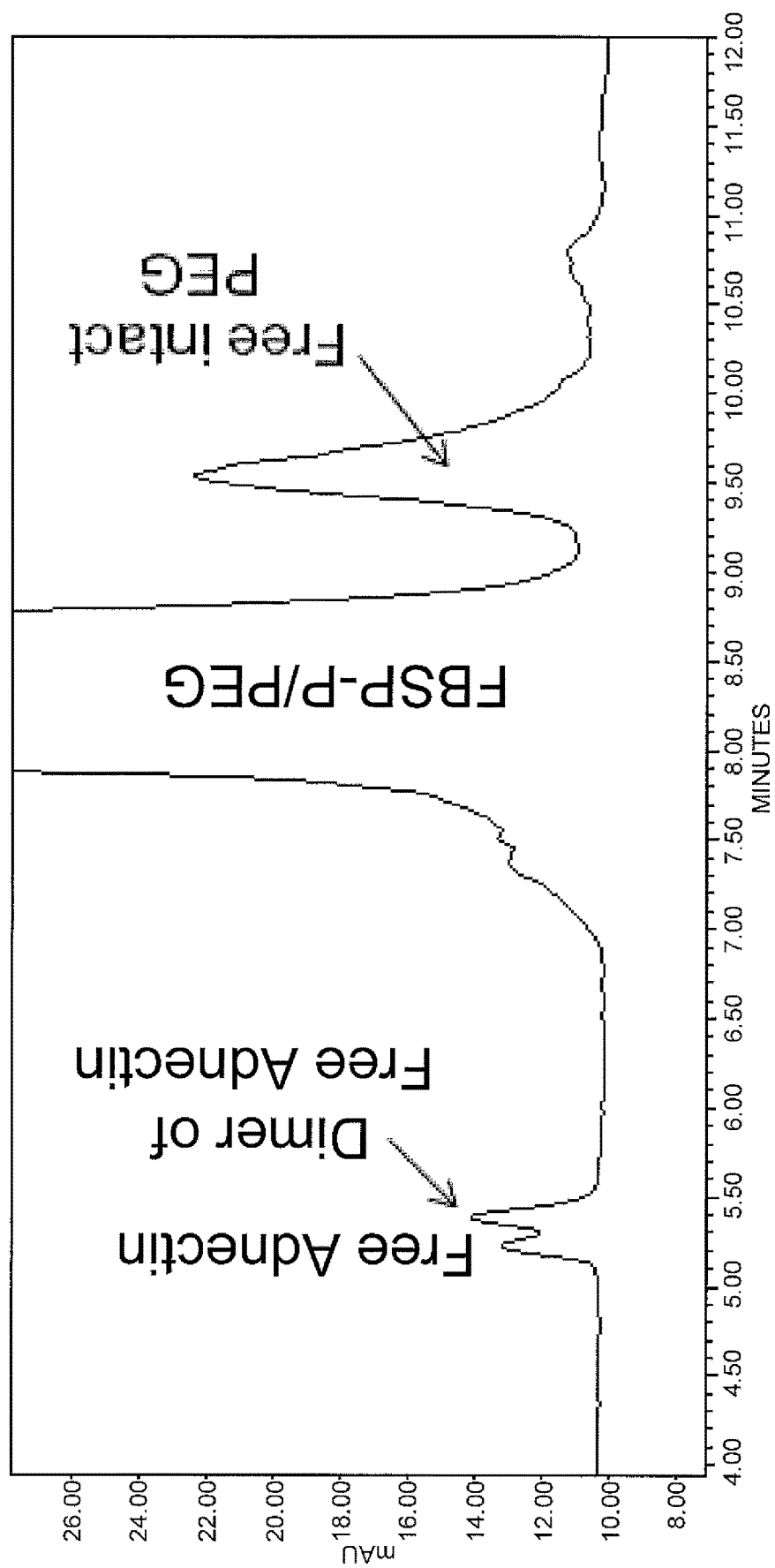

An exemplary fibronectin-based scaffold protein is FBSP-P, which is a mono-ADNECTIN™ having high affinity binding to PCSK9. FBSP-P is conjugated to a 40 kDa branched PEG via a lone cysteine residue on the protein. During formulation development of FBSP-P, an initial pH range of 6.0 to 7.5 was examined since, at the time, a neutral pH was thought to be desirable for the subcutaneous administration of the product. An example of the RP-HPLC results can be seen in FIG. 2. Samples were run on a Polymer Labs PLRP-S column, 2.0*150 mm, with a column temperature of 40° C. and an $H_2O$/ACN/TFA gradient. Dual detection was performed with UV and Evaporative Light Scattering (ELS), which measures a relative quantification of protein-related impurities by UV signal and quantifies free PEG species by ELS signal using a PEG calibration curve.

Figure 3:
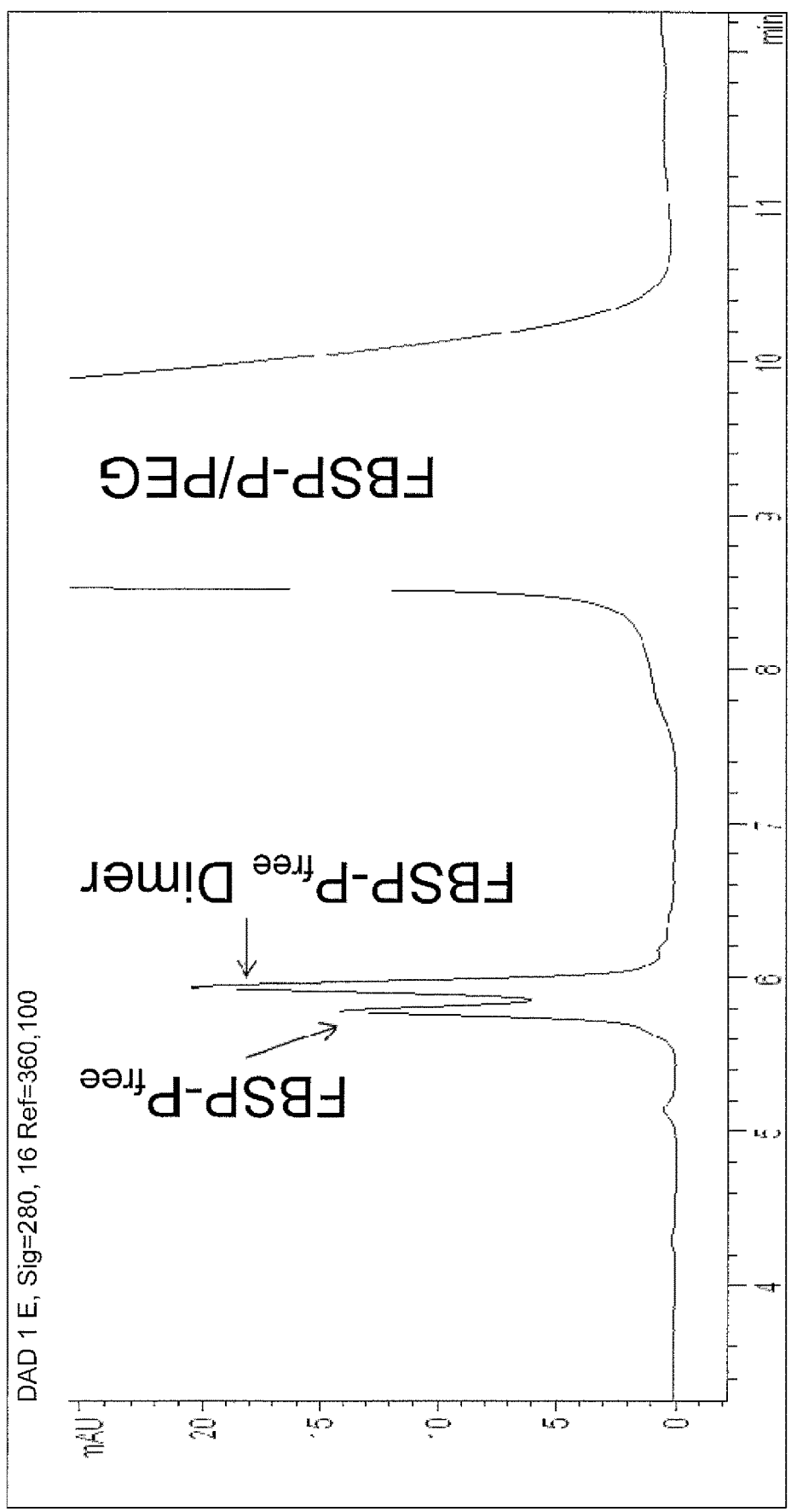
FIG. 3 shows UV (280 nm) profile of a FBSP-P stability sample (1 mg/mL, formulated in 25 mM succinate, 1% glycine, pH 7.5; incubated at 25° C. for two weeks) from an LC-MS analysis.

From the preliminary data of the pH screen, an increase in the level of free PEG and protein fragments was observed as a function of increasing pH. Characterization of the protein fragments was performed by LC-MS, which identified these species to be that of the intact, free (unPEGylated) FBSP-P ADNECTIN™ and its covalent dimer (FIG. 3 and Table 1).

Unlike previous ADNECTIN™ molecules, FBSP-P showed no clipping along its protein backbone due to the substitution of the aspartic acid in the C-terminal tail region with a glutamic acid at the position corresponding to amino acid residue 97 of SEQ ID NO: 47 (i.e., a DK-construct). Although several other aspartic acid residues exist in the protein sequence, these did not lead to clipping and only the fragment peaks identified in FIG. 3 and Table 1 were consistently observed during formulation development and stability.

Figure 4:
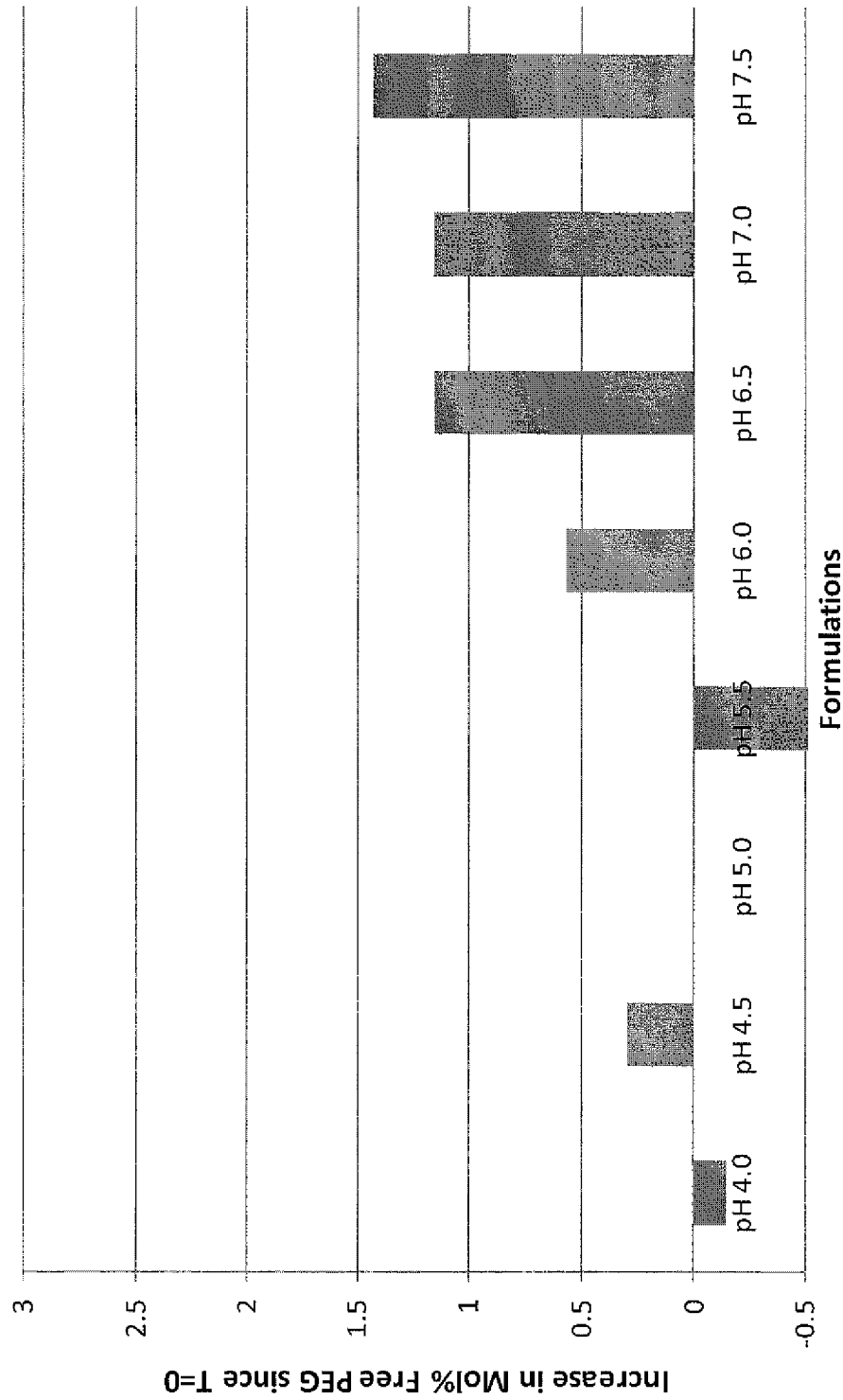
FIG. 4 presents a graph showing an increase in mole % of free PEG in FBSP-P samples formulated at different pH, during 25° C. stability testing for two weeks. Protein was formulated at 1 mg/mL in 25 mM succinate, 5% (w/v) sorbitol, at the pH indicated.
Figure 5:
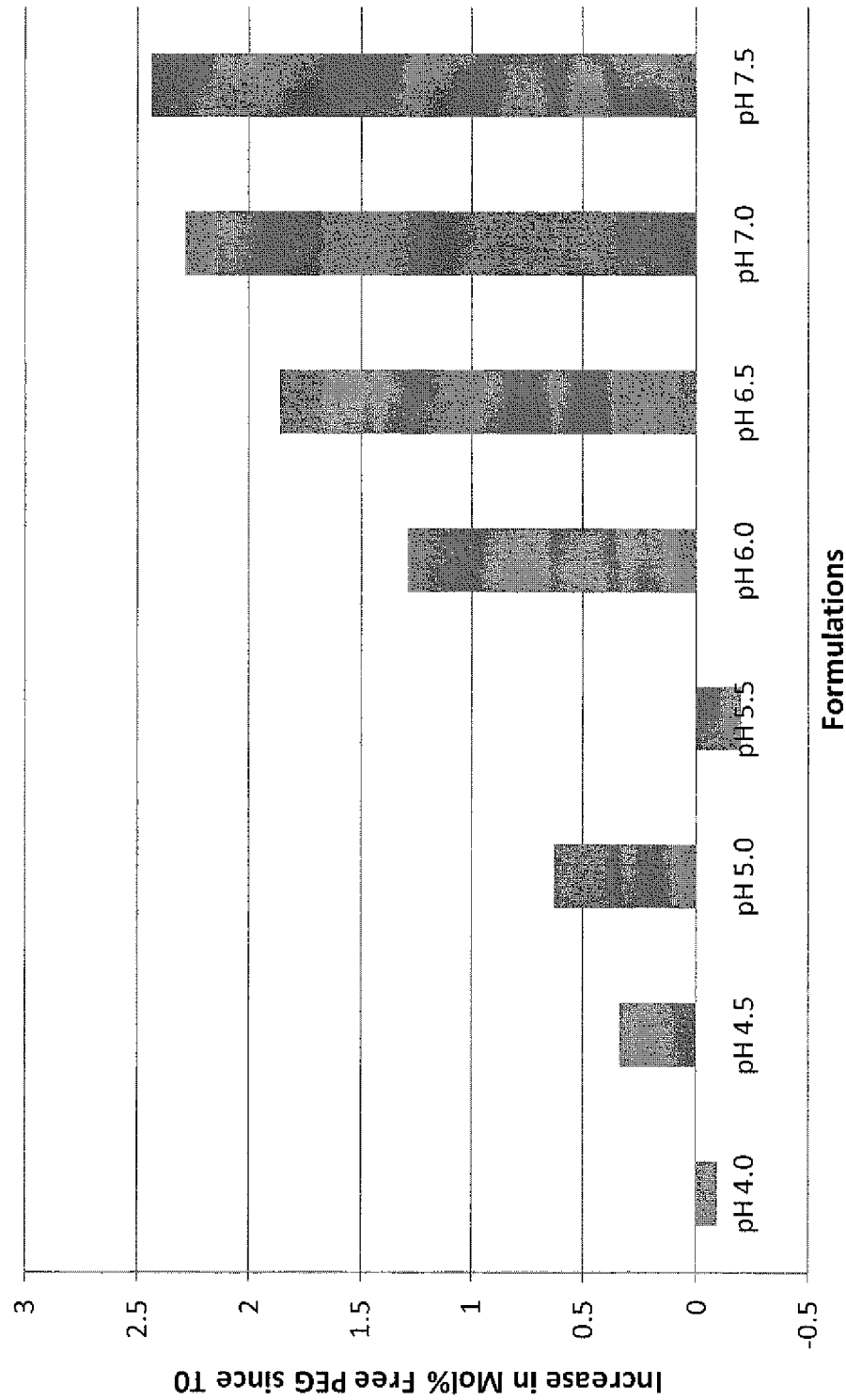
FIG. 5 is a graph showing an increase in mole % of free PEG in FBSP-P samples formulated at different pH, during 37° C. stability testing for two weeks. Protein was formulated at 1 mg/mL in 25 mM succinate, 5% (w/v) sorbitol, at the pH indicated.

With the fragmented species characterized, and no other clipped species observed, this was the first occasion where dePEGylation could be clearly identified in ADNECTINS™. Based on these preliminary data, a lower pH range of 4 to 6 was examined for dePEGylation, and the complete set of results covering the entire pH range of 4 to 7.5 can be seen in FIG. 4 and FIG. 5, where the mole % of free PEG detected is plotted as % increase since T=0. In FIGS. 4 and 5, data have been normalized for more direct comparison since two different batches of FBSP-P drug substance were used in the experiments, with the earlier lot showing a higher initial level of free PEG and free ADNECTIN™. The negative values were likely a result of assay variability and the low level of free PEG in these samples.

Figure 6A:
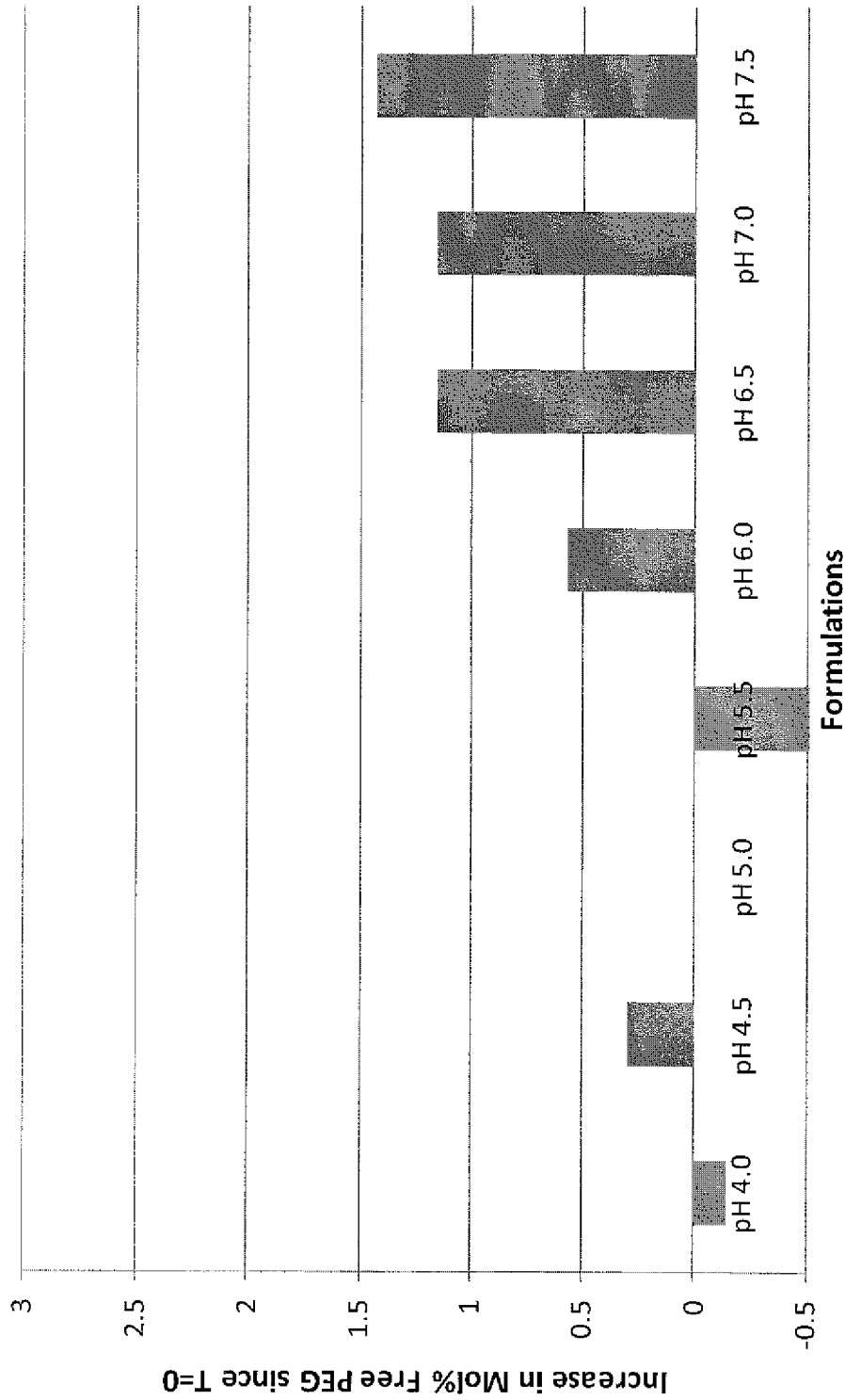
FIG. 6A-B shows the increase in % free (unPEGylated) ADNECTIN™ in FBSP-P samples formulated at different pH, during 25° C. stability testing for two weeks. Free ADNECTIN™ refers to the sum of both the monomeric and dimeric form of the unPEGylated protein. Protein was formulated at 1 mg/mL in 25 mM succinate, 5% (w/v) sorbitol, at the pH indicated.
Figure 6B:
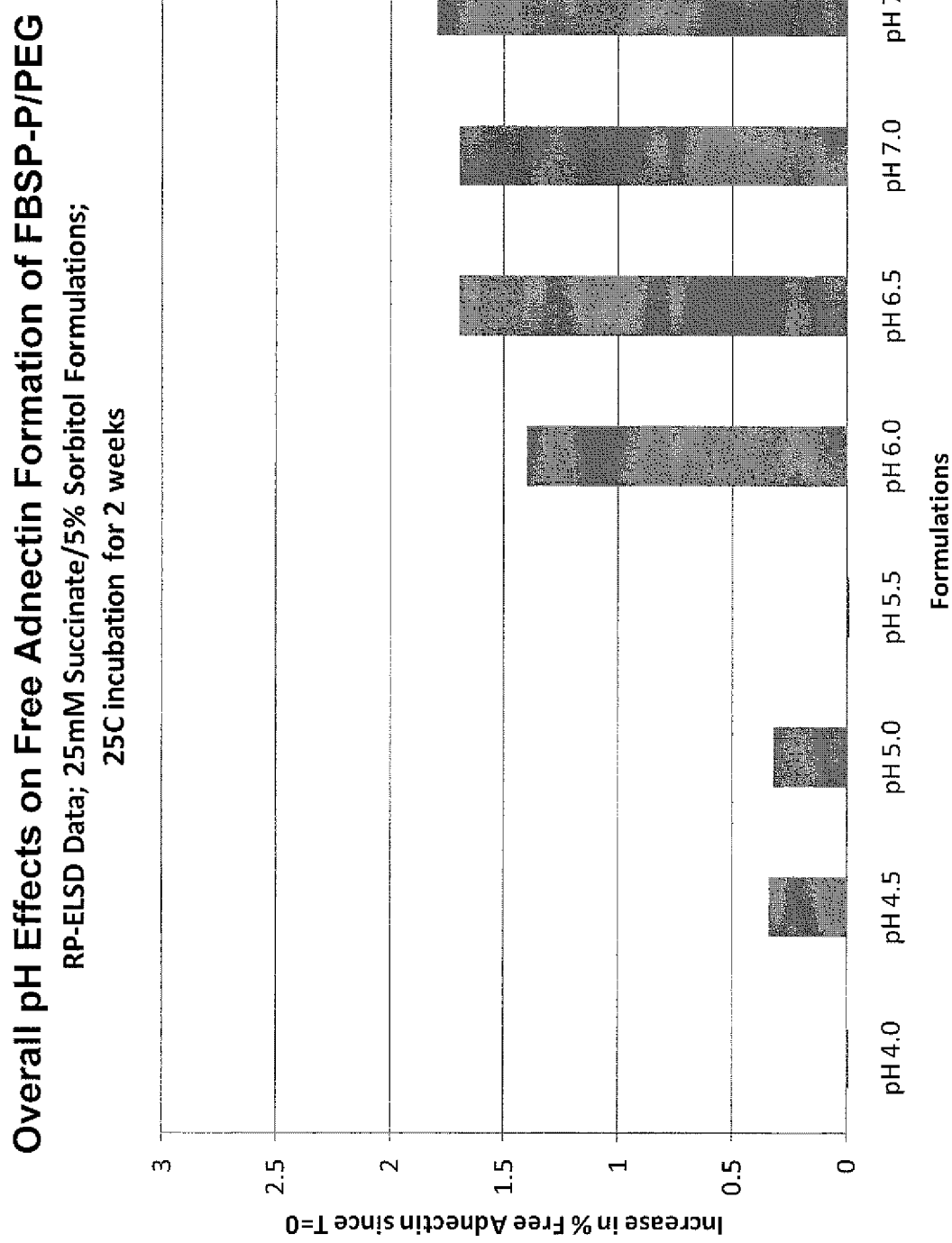
Figure 8A:
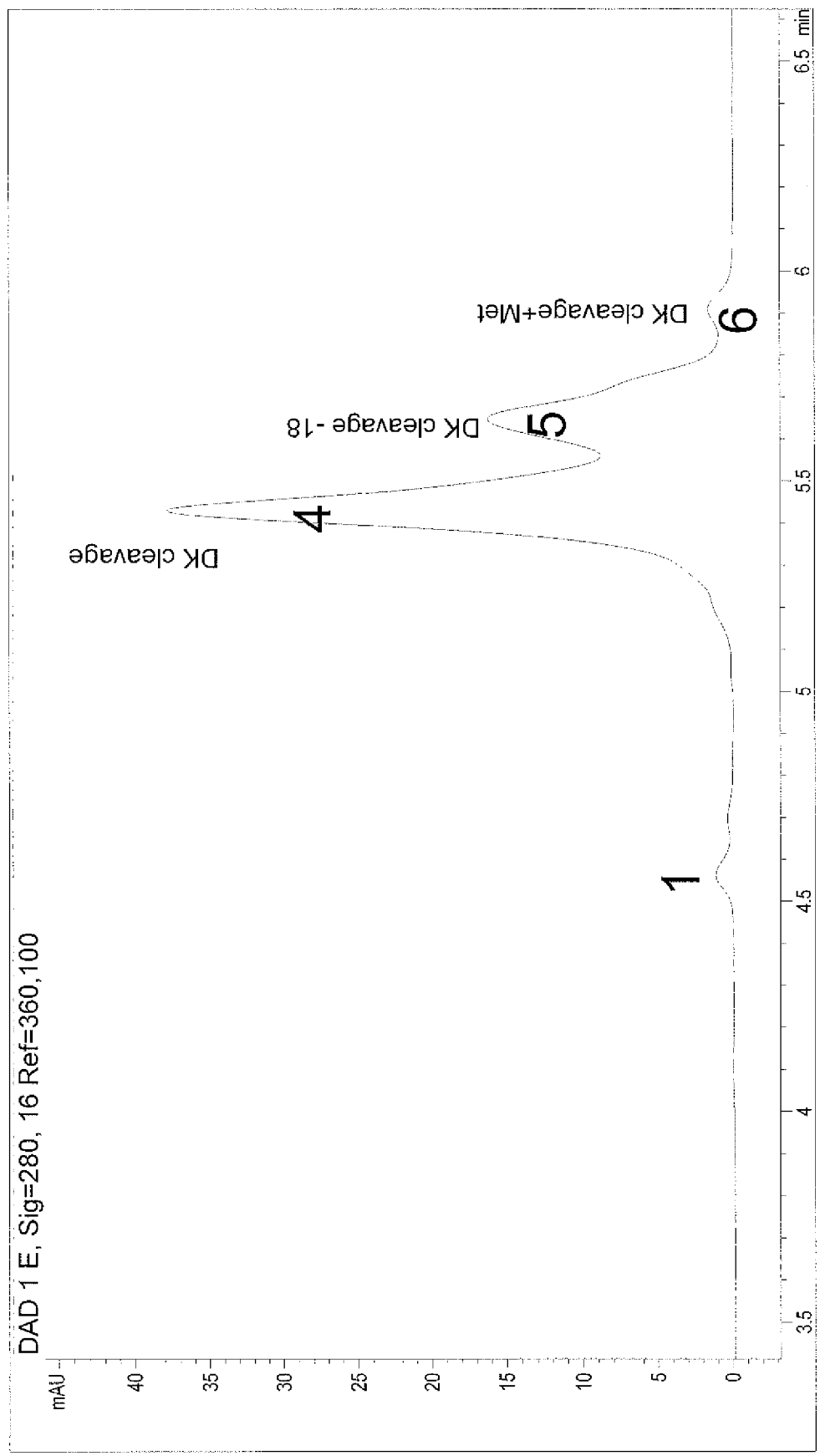
FIG. 8A-D is a series of UV profiles (at 280 nm) of FBSP-V stressed samples at different pH values, obtained from LC-MS analysis. FBSP-V$_{free}$ refers to the free (unP-EGylated) ADNECTIN™ of FBSP-V. Only the pre-peak region of the UV profile is shown. All samples (10 mM sodium acetate, 5% mannitol) were stressed at 25° C. for a period of 6 months.
Figure 8B:
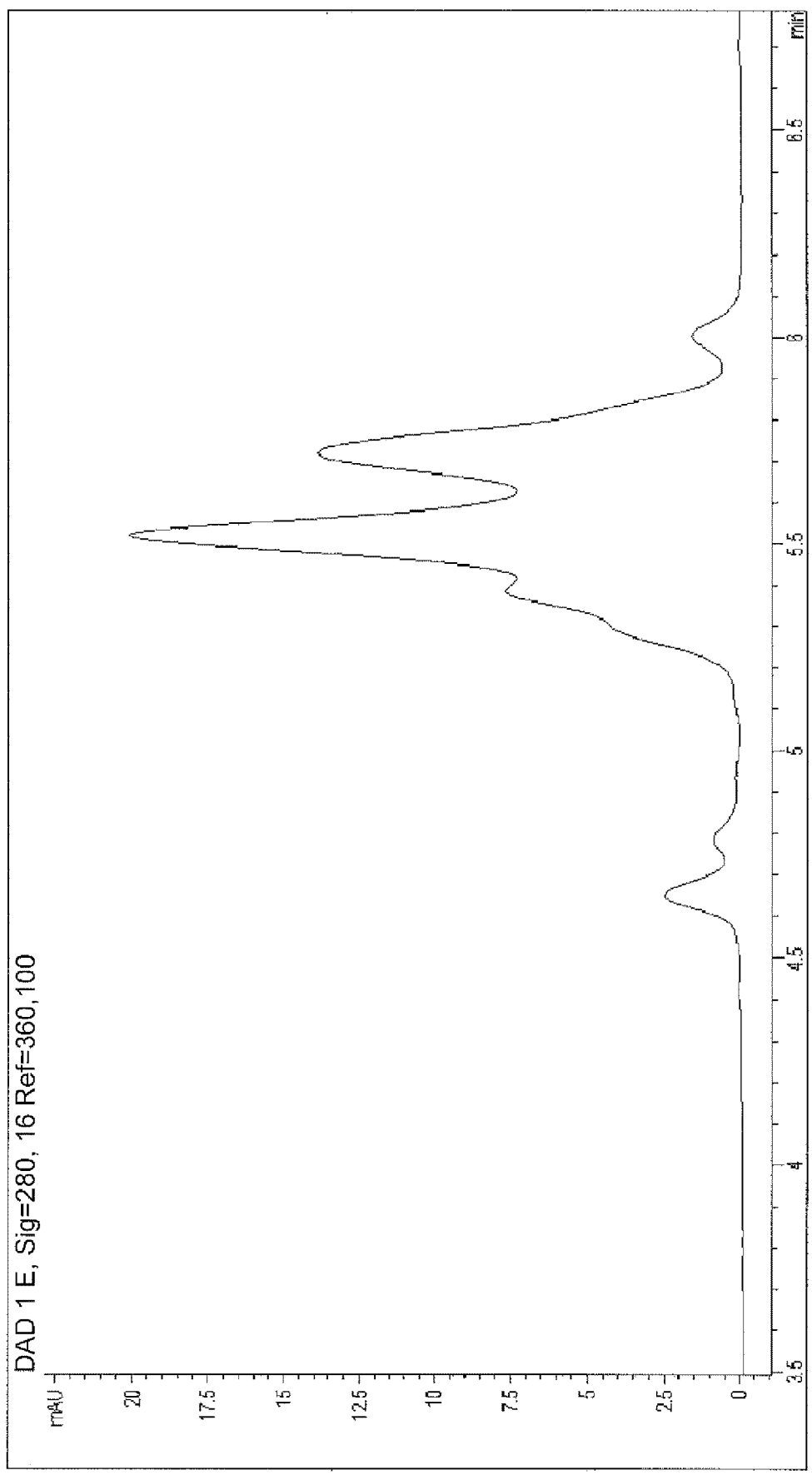
Figure 8C:
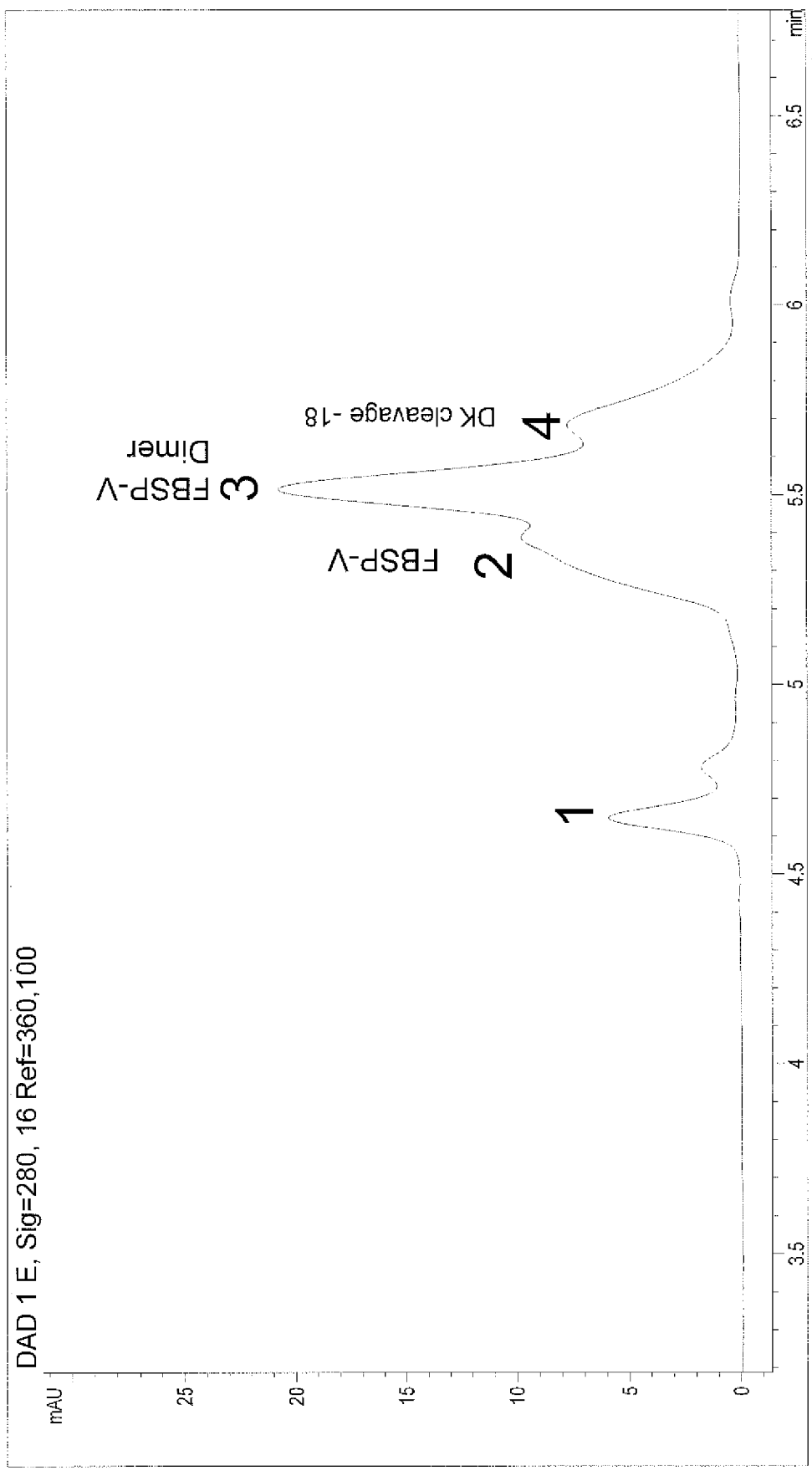
Figure 8D:
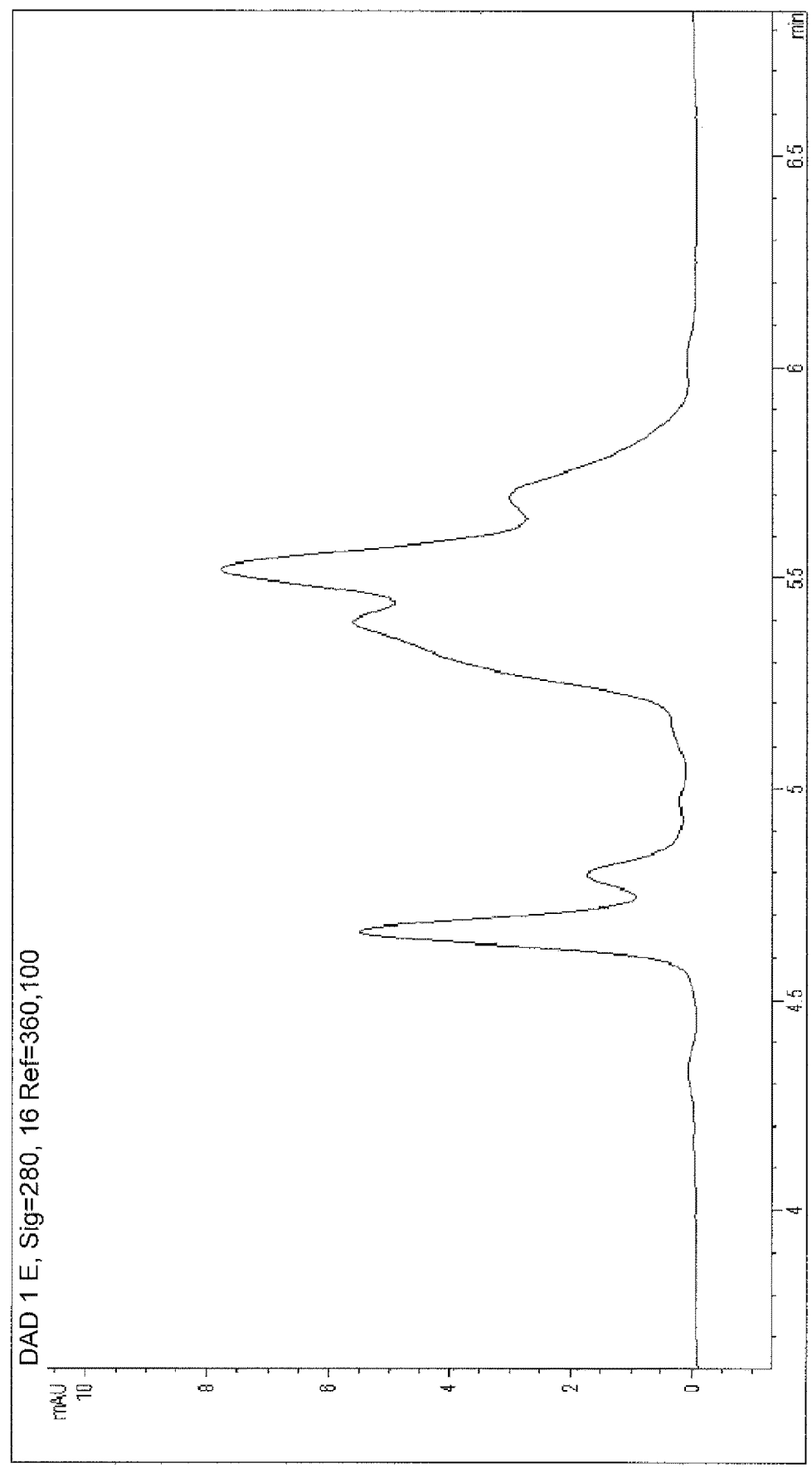

From the data presented above, a clear pH dependency can be seen in the level of dePEGylation. In the lower pH formulations, some instances of decreased levels of free PEG can be seen, which was likely attributed to the very low levels of free PEG detected along with variability with the ELS detection. Since the balance of dePEGylation is the free (unPEGylated) ADNECTIN™, the pH effect on the formation of that species is also evaluated and this is presented in FIG. 6 and FIG. 7.

Increased levels of free PEG and free (unPEGylated) ADNECTIN™ correlate very well to each other, at two elevated temperatures, with both showing a pH dependency.

Example 2

Long-Term Stability and Formulation Study of FBSP-V

Following the discovery of dePEGylation with certain formulations of FBSP-P, other ADNECTINS™ were examined to determine if they were subject to the same degradation. FBSP-V is an ADNECTIN™ that binds to VEGFR2 with high affinity and having the sequence of SEQ ID NO: 48. FBSP-V is conjugated to a 40 kDa branched PEG moiety via a lone cysteine residue at position 93 of SEQ ID NO: 48. DePEGylation of FBSP-V was evaluated using a set of formulations ranging from pH 4.5 to 6.5. Similar to FBSP-P, the free (unPEGylated) FBSP-$V_{free}$ ADNECTIN™ was evident in these samples and its relative level also increased as a function of increasing pH. The LC-MS results of the most degraded sample at pH 6.5 are shown in FIG. 8 and Table 2. Relative quantification of these fragmented species can be seen in Table 3.

With FBSP-V containing a DK in the C-terminal tail region (i.e., the aspartic acid at position 90 of SEQ ID NO: 48), two additional clips were also observed which represented cleavage at the aspartic acid at position 90. As previously established with other ADNECTIN™ molecules, formulations at lower pH leads to higher level of DK cleavages. The data in Table 3 indicates this trend in regard to total pre-peaks; however, as the pH increases, the % of intact free ADNECTIN™ increases, which was the same trend as that observed in FBSP-P as described in Example 1.

Figure 9:
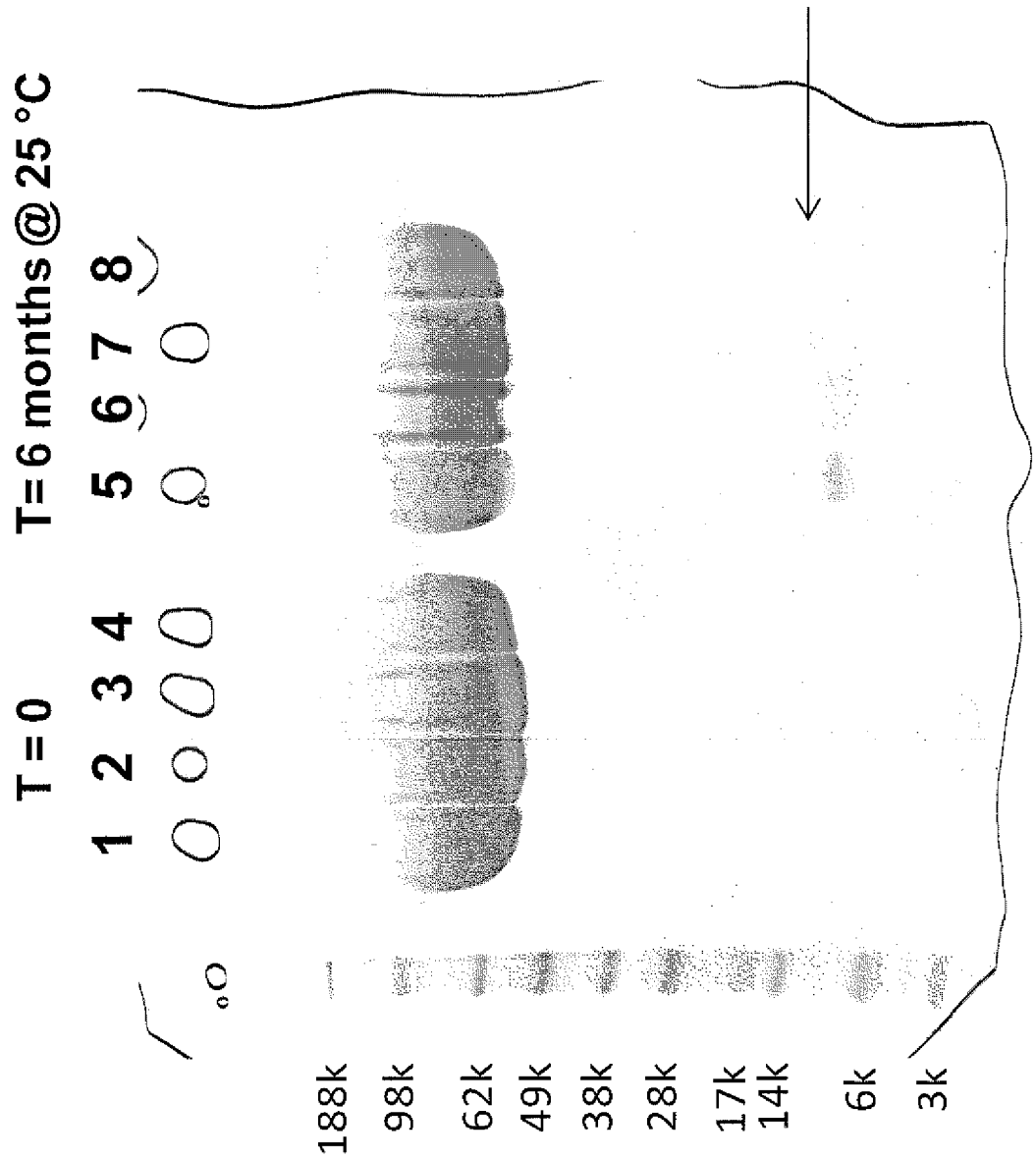
FIG. 9 illustrates the results of non-reduced SDS-PAGE analysis of FBSP-V stability samples at T=0 and T=6 months at 25° C. Lanes 1 and 5 are FBSP-V formulated in 10 mM sodium acetate, 2% mannitol, 100 mM sodium chloride, pH 4.5 at 5 mg/mL. Lanes 2 and 6 are each FBSP-V formulated in 10 mM sodium acetate, 5% mannitol, pH 4.5, at 5 mg/mL protein concentration. Lanes 3 and 7 are FBSP-V formulated in 10 mM sodium acetate, 5% mannitol, pH 5.5, at 5 mg/mL protein concentration. Lanes 4 and 8 are FBSP-V formulated in 10 mM sodium acetate, 5% mannitol, pH 6.5, at 5 mg/mL protein concentration. All FBSP-V lanes were loaded equally at 10 µg each. The arrow indicates the presence of a band corresponding to the free FBSP-V$_{free}$ ADNECTIN™.

Analysis of the same FBSP-V stability samples by SDS-PAGE revealed similar information in a qualitative manner (FIG. 9). For stressed samples at the lowest pH (pH 4.5, in lanes 5 and 6), a clipped species can be seen above the 6 kD MW marker, corresponding to the dominant clip (G2-D91, corresponding to residues 1-90 of SEQ ID NO: 48). The presence of sodium chloride in the sample showed a higher level of this clip as compared to the sample formulated without sodium chloride at the same pH. As the pH of the formulation increased, this clip decreased in intensity but another band at slightly higher molecular weight now appeared, corresponding in molecular weight to the free FBSP-$V_{free}$ ADNECTIN™ at just above 10 kD. Moreover, the new band (indicated with an arrow) appeared to increase in intensity as the formulation pH increased from 5.5 to 6.5. These observations are consistent with those described in FIG. 8, Table 2 and Table 3.

Example 3

Characterization of FBSP-V/I

Another exemplary fibronectin-based scaffold protein is FBSP-V/I, a multivalent polypeptide with high affinity to VEGFR2 and IGF-IR. FBSP-V/I comprises the amino acid sequence of SEQ ID NO: 9, and contains a single 40 kDa branched PEG conjugated to the cysteine at position 203 of SEQ ID NO:9.

Figure 10:
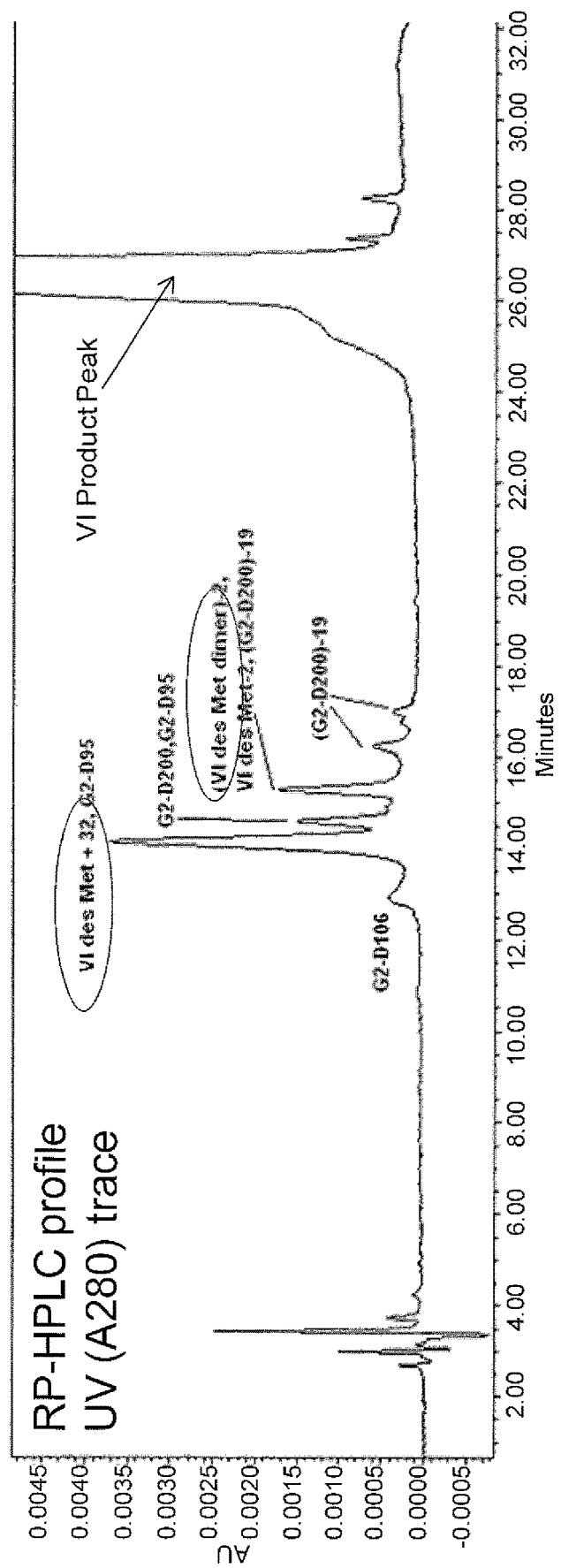
FIG. 10 is the UV profile (280 nm) of a stressed FBSP-V/I sample (10 mM acetate, 150 mM sodium chloride, pH 5.5, 5 mg/mL; 25 C for 4 weeks). Peak assignments shown were based on LC-MS analysis.

Characterization of a stressed FBSP-V/I sample is shown in FIG. 10. The results demonstrate, among various protein clips, the existence of the intact free (unPEGylated) FBSP-V/I ADNECTIN™ in the des Met form with oxidation (+32). The dimeric form of the same species can also be seen.

For a sample with the following sequence (SEQ ID NO: 9):

```
MGVSDVPRDL EVVAATPTSL LISWSARLKV ARYYRITYGE

TGGNSPVQEF TVPKNVYTAT ISGLKPGVDY TITVYAVTRF

RDYQPISINY RTEIDKPSTS TSTVSDVPRD LEVVAATPTS

LLISWRHPHF PTRYYRITYG ETGGNSPVQE FTVPLQPPTA

TISGLKPGVD YTITVYAVTD GRNGRLLSIP ISINYRTEID

KPCQ
```

Several D residues are involved in fragmentation (in bold, italic font), with D95 and D200 (underlined) being the primary sites. With heat stress, cleavage also occurs at the maleimide bond of the PEG conjugation, resulting in the release of free FBSP-V/I (shown as "VI des Met").

Figure 11:
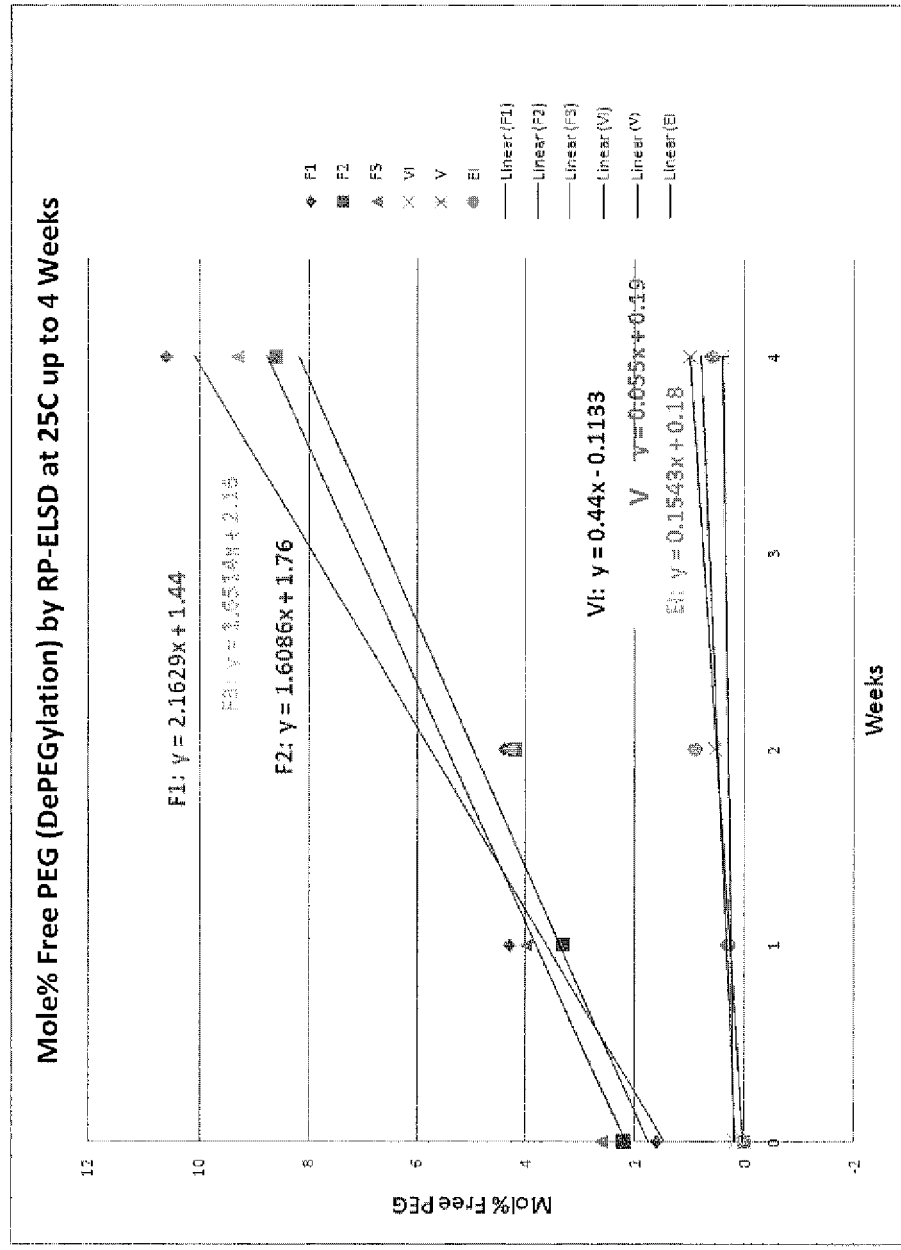
FIG. 11 shows a comparison of dePEGylation in several ADNECTINS™, as a measure of free PEG over the course of 1-4 weeks. The exemplary ADNECTINS™ are FBSP-P (samples F1, F2, and F3) stored at pH6.0; FBSP-V/I stored at pH 5.5 (VI); FBSP-V stored at pH 5.0 (V); and FBSP-E/I stored at pH 4.0 (EI).

FIG. 11 shows a comparison of dePEGylation of several ADNECTINS™, as a measure of free PEG over the course of 1-4 weeks. The exemplary ADNECTINS™ are FBSP-P (samples F1, F2, and F3) stored at pH 6.0; FBSP-V/I stored at pH 5.5; FBSP-V stored at pH 5.0; and FBSP-E/I stored at pH 4.0. FBSP-E/I is a multivalent polypeptide comprising two $^{10}$Fn3 domains with the BC, DE and FG loops altered such that one $^{10}$Fn3 domain binds with high affinity to EGFR and the other $^{10}$Fn3 domain binds with high affinity to IGF-IR.

Example 4

Characterization of Free PEG

A question arose as to the exact structure and functionality of the free PEG lost from the ADNECTINS™ during stability. Based on elution time by RP-HPLC, the free PEG peak appeared to closely resemble the unstressed PEG in terms of hydrophobicity, which would imply that the liberated free PEG remained largely intact and was close in molecular weight and size to the unstressed PEG.

The preferred pH range for conjugation through maleimide chemistry is 6.5 to 7.5, and in the past the PEGylation step for ADNECTINS™ has been conducted at pH 5 to 5.5 using the PEG in solid form. To address functionality, PEG solutions were prepared using MILLI-Q® water (pH~5.5) and 50 mM Tris (pH 7.0). The solutions were stressed at 37° C. for one week, and their functionality was assessed through a PEGylation reaction with the FBSP-V$_{free}$ ADNECTIN™. The pH 7 solution was pH adjusted to ~5.5 prior to the reaction for a more direct comparison to the PEG in water. The data in Table 4 shows that, after stress, some of the maleimide functional group on the PEG was lost in the pH 5.5 solution and that the functionality was completely lost in the pH 7.0 solution.

TABLE 1

Summary of MS results on the protein fragments shown in FIG. 3. The molecular weight of FBSP-P cannot be determined due to the heterogeneity associated with the PEGylation.

| Peak Retention Time (min) | Observed MW (Da) | Theoretical MW (Da) | % Difference from Theoretical MW | Structure |
|---|---|---|---|---|
| 5.7 | 11337.3 | 11338.72 | −0.01 | Des Met form of FBSP-P$_{free}$ (G2-A104) |
| 6.0 | 22670.1 | 22675.44 | −0.02 | Des Met form of FBSP-P$_{free}$ dimer (disulfide linked) |

TABLE 2

Summary of MS results on the protein fragments shown in FIG. 8.

| Peak Retention Time (min) | Observed MW (Da) | Theoretical MW (Da) | % Difference from Theoretical MW | Structure |
|---|---|---|---|---|
| 4.6 | 6866 | 6868.7 | −0.04 | I28-D91 |
| 5.3 | 10361 | 10362.7 | −0.02 | FBSP-V$_{free}$ ADNECTIN™ (des Met form) |
| 5.5 | 20723 | 20723.4 | 0.00 | FBSP-V$_{free}$ ADNECTIN™ dimer (des Met form) |
| 5.7 | 9888 | 9888.2 | 0.00 | (G2 to D91)-water (DK cleavage product) |

TABLE 3

Relative quantification of protein fragments in FBSP-V stressed samples. Quantification is based on total UV area at 280 nm including the FBSP-V product peak. "Total pre-peaks" refers to all pre-peaks detected before the elution of FBSP-V product including all clips and intact FBSP-V$_{free}$ species; "free FBSP-V$_{free}$ ADNECTIN™" refers to the sum of free (unPEGylated) FBSP-V$_{free}$ ADNECTIN™ and FBSP-V$_{free}$ dimer.

| FBSP-V Formulation | Total % Pre-peaks (Clips + FBSP-V$_{free}$ ADNECTIN™) | % Free FBSP-V$_{free}$ ADNECTIN™ Only | Mol % Free PEG |
|---|---|---|---|
| 10 mM Sodium Acetate, 5% mannitol, pH 4.5; 5 mg/mL | 7.0% | 0.0% | 0.63 |
| 10 mM Sodium Acetate, 5% mannitol, pH 5.5; 5 mg/mL | 2.9% | 1.7% | 1.01 |
| 10 mM Sodium Acetate, 5% mannitol, pH 6.5; 5 mg/mL | 2.7% | 1.9% | 1.60 |
| 10 mM Sodium Acetate, 5% mannitol, pH 6.5; 10 mg/mL | 3.3% | 2.4% | 1.56 |

TABLE 4

Conjugation efficiency of 40k PEG maleimide after heat and pH stresses

| Stress Conditions | % Unconjugated FBSP-V$_{free}$ ADNECTIN™ | |
|---|---|---|
| | PEG in MQ water (pH ~5.5) | PEG in 50 mM Tris (pH 7.0) |
| T = 0 | 15.9% | 15.9% |
| T = 1 week, 37 C. | 33.1% | 100% |

Materials and Methods

Materials

FBSP-P. Two lots of FBSP-P (lots 1 and 2) were used in two separate pH studies covering the range of pH 4 to 7.5, at half pH unit intervals. The samples were formulated using the high throughput formulation format on a TECAN® robot. The drug substance (10 mg/mL, in 10 mM succinate, pH 6.0) was mixed with concentrates of succinate buffers (from pH 4 to 7.5) and sorbitol, which resulted in a final protein concentration of 1 mg/mL or 10 mg/mL in the excipients and pH described in the results section. The samples were put on stability in 96-well plate format and tested directly out of the plates.

FBSP-V/I. The FBSP-V/I sample was formulated using tangential flow filtration (TFF), filled in vials and subject to stability testing as described herein.

FBSP-V. The samples were formulated by TFF into the buffers indicated, filled in vials and subject to stability testing as described herein.

Analytical Methods

RP-UV-ELSD. A PLRP-S column (4.6*150 mm, Polymer Labs) was used for the analysis of FBSP-P samples. The protein fragments were analyzed on a relative percent basis at 280 nm using UV detection, and the free PEG moiety was quantified on a mole % basis using a 5-point PEG calibration curve with evaporative light scattering (ELS) detection. The method utilizes a water/acetonitrile/trifluoroacetic acid gradient.

RP-UV. A Jupiter C18 column (4.6*250 mm, PHENOMENEX®) was used for the analysis of FBSP-V and FBSP-V/I samples. The protein fragments were analyzed on a relative percent basis at 280 nm using UV detection. The method utilizes a water/acetonitrile/trifluoroacetic acid gradient.

LC-MS. The HPLC method using the Jupiter C18 column was coupled to a Thermo LTQ ion trap mass spectrometer, and the flow was split after the UV detector with 0.2 mL/min introduced into the ionization source of the MS. The MS data obtained was deconvoluted using the MagTran software, and structures were assigned to the detected masses using the PAWS software.

Expression, PEGylation and Purification of Fibronectin Based Scaffold Proteins (FBSP)

For expression of FBSP, a nucleotide sequence encoding the construct is cloned into an inducible expression vector and is expressed in *E. coli* cells (either as a soluble fraction or into intracellular inclusion bodies). Cell bank vials generated from a culture of a single plated colony are used to inoculate a shake flask culture as an inoculum for a large-scale fermentor. Alternatively, a seed fermentor is used for an inoculum culture, depending on the final fermentation volume. The large-scale fermentation contains a growth phase to accumulate biomass and a production phase to generate the FBSP.

For insoluble FBSP, intracellular inclusion bodies are released from harvested cells using a MICROFLUIDIZER® and recovered by centrifugation, followed by washes with buffer and water. The purification process for insoluble FBSP uses a Guanidine-HCl based resolubilization of inclusion bodies, followed by refolding the protein.

For soluble FBSP, cells were pelleted and lysed using a MICROFLUIDIZER® and the soluble fraction was recovered by centrifugation, and the supernatant was clarified by filtration.

The protein is then purified using one or more columns, such as a HISTRAP® column, a cation exchange chromatography column, and/or a hydrophobic interaction column. The resulting purified FBSP is then covalently linked to a PEG via maleimide chemistry at a single cysteine residue to produce PEGylated protein.

The PEGylated protein may then be purified over one or more additional columns, such as a cation exchange chromatography column. The elution is concentrated to a target protein concentration and then exchanged into the formulation buffer using ultrafiltration/diafiltration (UF/DF). The UF/DF product is filtered using a final 0.22 µm filter. The filtered product is then filled into vials to produce the final product.

Example 5

DePEGylation of Short PEGylated Peptides

This Example shows that dePEGylation at neutral or alkaline pH occurs not only with polypeptides and proteins, but also with smaller peptides. This Example also shows that dePEGylation occurs regardless of the type of linker connecting the PEG moiety to the peptide and regardless of the type of PEG.

Figure 12:
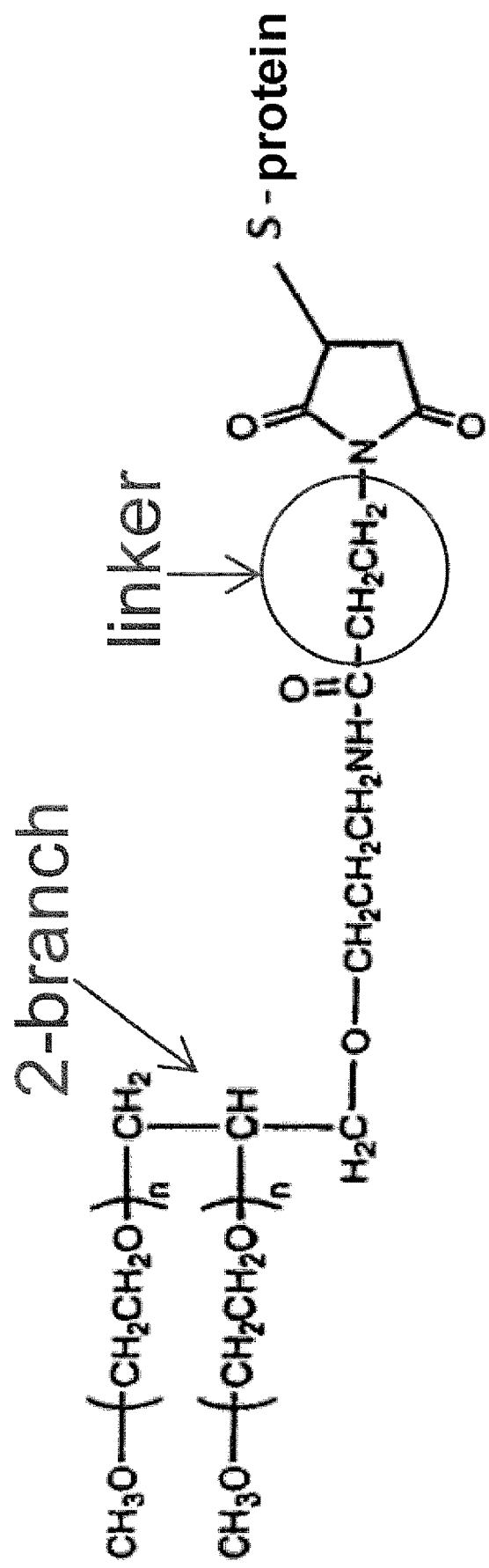
FIG. 12 shows the structure of a 2-branched PEG-MAL with a C2 alkyl linker, conjugated to a protein through cysteine residue.

A synthetic peptide, TEIEKPCQ (SEQ ID NO: 49), bearing the same C-terminal sequence as wildtype $^{10}$FN3 proteins, was utilized as a model peptide for conjugation to three different 40 kD PEG-MALs at its penultimate cysteine residue. The structures of the three PEG-MALs are described below:

2-Branched PEG-MAL, with a C2 alkyl linker (NOF p/n Sunbright GL2-400MA; FIG. 12)

2-Branched PEG-MAL, with a C5 alkyl linker (NOF p/n Sunbright GL2-400MA3)

Linear PEG-MAL, with a C2 alkyl linker (NOF p/n Sunbright ME-400MA) The PEG conjugated peptides were purified using PD-10 columns and formulated into 1× PBS at pH 8.3. The formulated peptides were analyzed at T=0 and then at 1 week after heat stress at 37° C. for level of dePEGylation.

The samples were analyzed for dePEGylation by RP-HPLC. A Polaris C8-A column (2.1*150 mm, VARIAN®) was used for the analysis of PEGylated peptide samples. The free peptide was quantified on a relative percent basis to the intact sample at 214 nm using UV detection. The method utilizes a water/acetonitrile/trifluoroacetic acid gradient. For peak identification, LC-MS was conducted.

Figure 13:
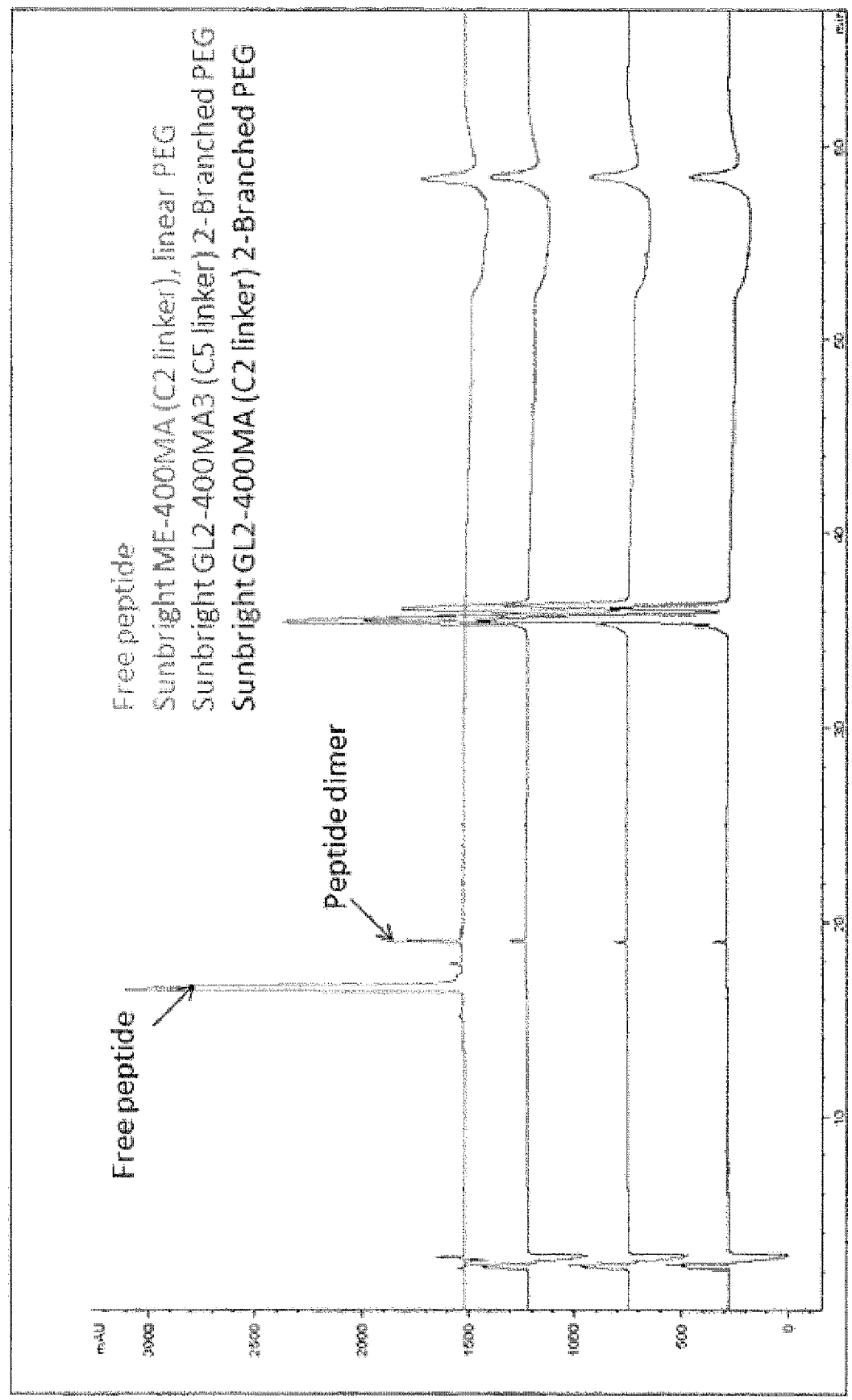
FIG. 13 shows HPLC profiles of a synthetic peptide conjugated to three different 40 kD PEG-MALs in a composition at pH 8.3 and at T=0. The profiles from top to bottom are those of: (1) free peptide; (2) peptide conjugated to ME-400MA (C2 linker) linear PEG; (3) peptide conjugated to GLE-400MA3 (C5 linker) 2-branched PEG; and peptide conjugated to GLE-400MA (C2 linker) 2-branched PEG.
Figure 14:
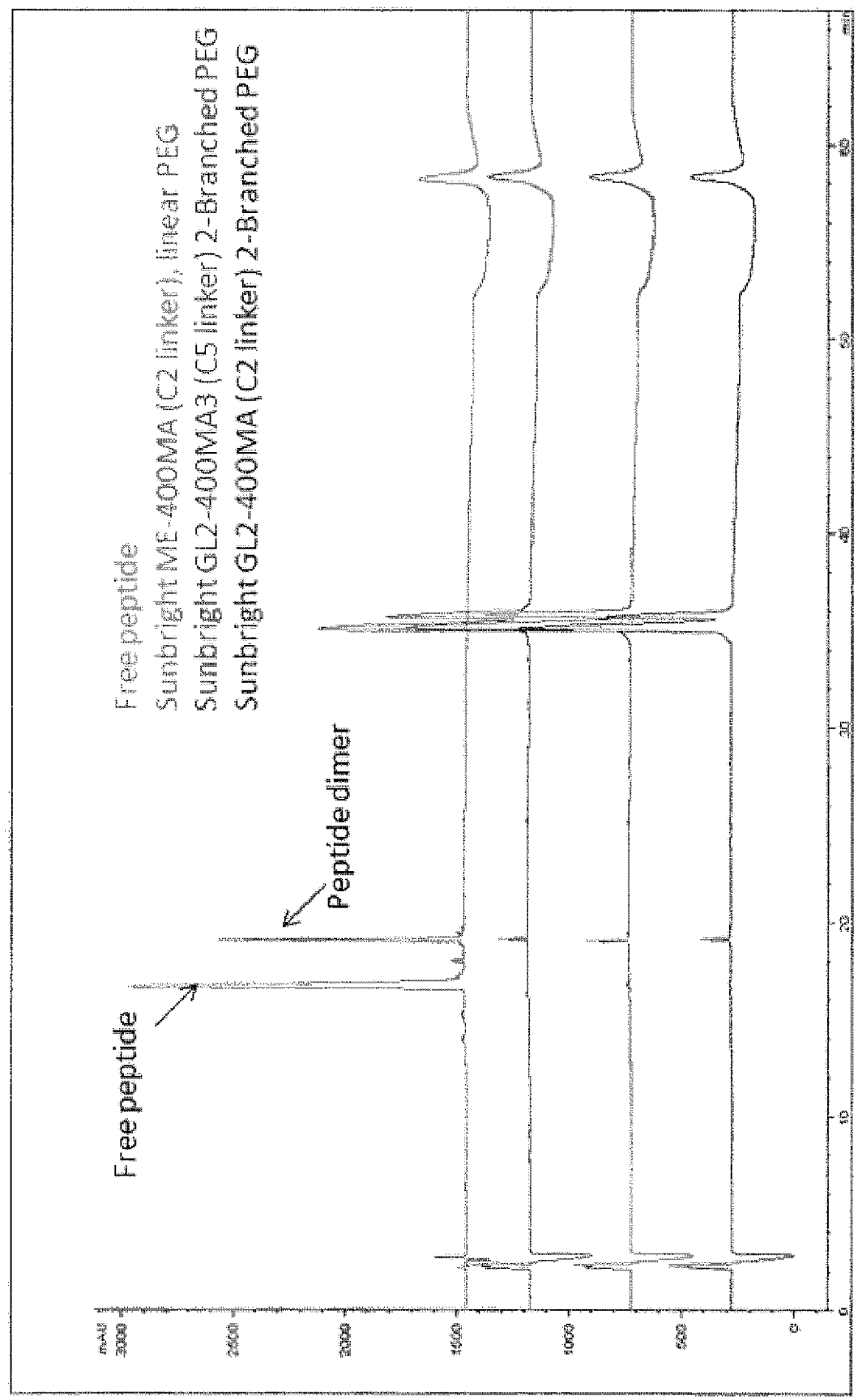
FIG. 14 shows HPLC profiles of a synthetic peptide conjugated to three different 40 kD PEG-MALs in a composition at pH 8.3 (same as in FIG. 13), after one week at 37° C. The profiles from top to bottom are those of: (1) free peptide; (2) peptide conjugated to ME-400MA (C2 linker) linear PEG; (3) peptide conjugated to GLE-400MA3 (C5 linker) 2-branched PEG; and peptide conjugated to GLE-400MA (C2 linker) 2-branched PEG.
Figure 15:
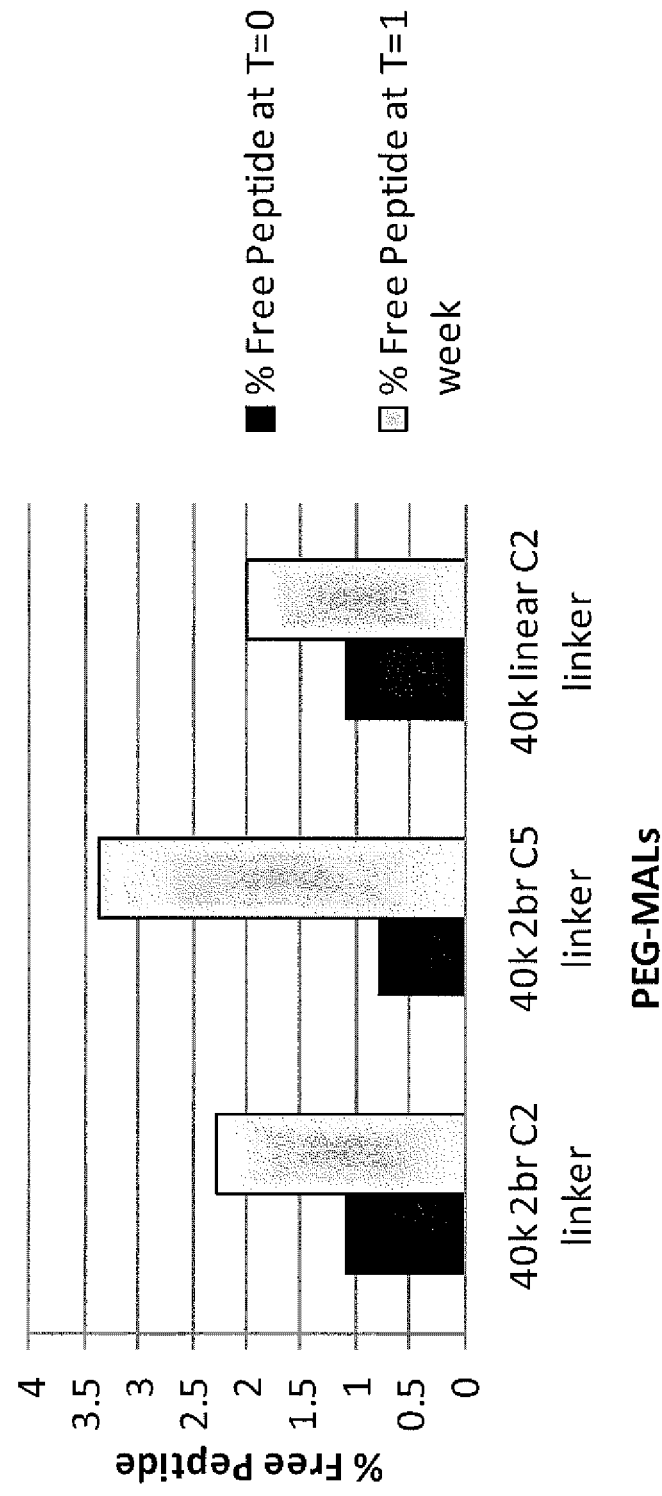
FIG. 15 shows the percentage of free peptide observed in samples of a peptide conjugated to three different 40 kD PEG-MALs in compositions at pH 8.3, at T0 and T=1 week after heat stress at 37° C. (histogram based on results shown in FIGS. 13 and 14).

The results, which are shown in FIGS. 13, 14 and 15, indicate that a higher level of dimerized free peptide was observed in each of the 3 stressed samples relative to the level in each of the samples at T=0. The bar graph in FIG. 15 demonstrates an increase in the relative level of the free peptide, in the form of a covalent dimer, for all three conjugated peptides after heat stress. The free peptide generated formed a covalent dimer due to the free cysteine now available as a result of dePEGylation, which was confirmed by MS and MS/MS analysis. The fact that the level of the covalent dimer increased after heat stress further indicates that the dePEGylation event regenerated an intact free peptide containing a free cysteine residue. A low level of the free peptide was present at T0 for all three samples due to its incomplete removal with the PD-10 column purification. However, a measurable increase in the level of the free peptide was still observed.

Thus, the results indicate that dePEGylation can also occur with a short peptide (i.e., not only with a larger polypeptide or protein). Moreover, the results show that dePEGylation is not greatly affected by the length of the alkyl linker, nor by the branching structure in the PEG-MAL, as all three samples underwent dePEGylation to a similar extent.

Example 6

Reduced DePEGylation of Small Peptide at Lower pH

This Example shows that less dePEGylation of a small PEGylated peptide occurs at lower pH relative to higher pH.

A synthetic peptide consisting of the amino acid sequence TEIDKPCQ (SEQ ID NO: 50)) was conjugated to a 2 kPEG-MAL. Briefly, the peptide was solubilized in NaOAc at pH 5.5. PEG in water was added to the peptide and the conjugation reaction occurred overnight. The sample was cleaned up via buffer exchange over PD-10 columns into pH 8.0 Tris or pH 5.5 NaOAc. The two samples were stressed at 37° C. for one week, followed by analysis using RP-HPLC, as described in Example 5.

Figure 16:
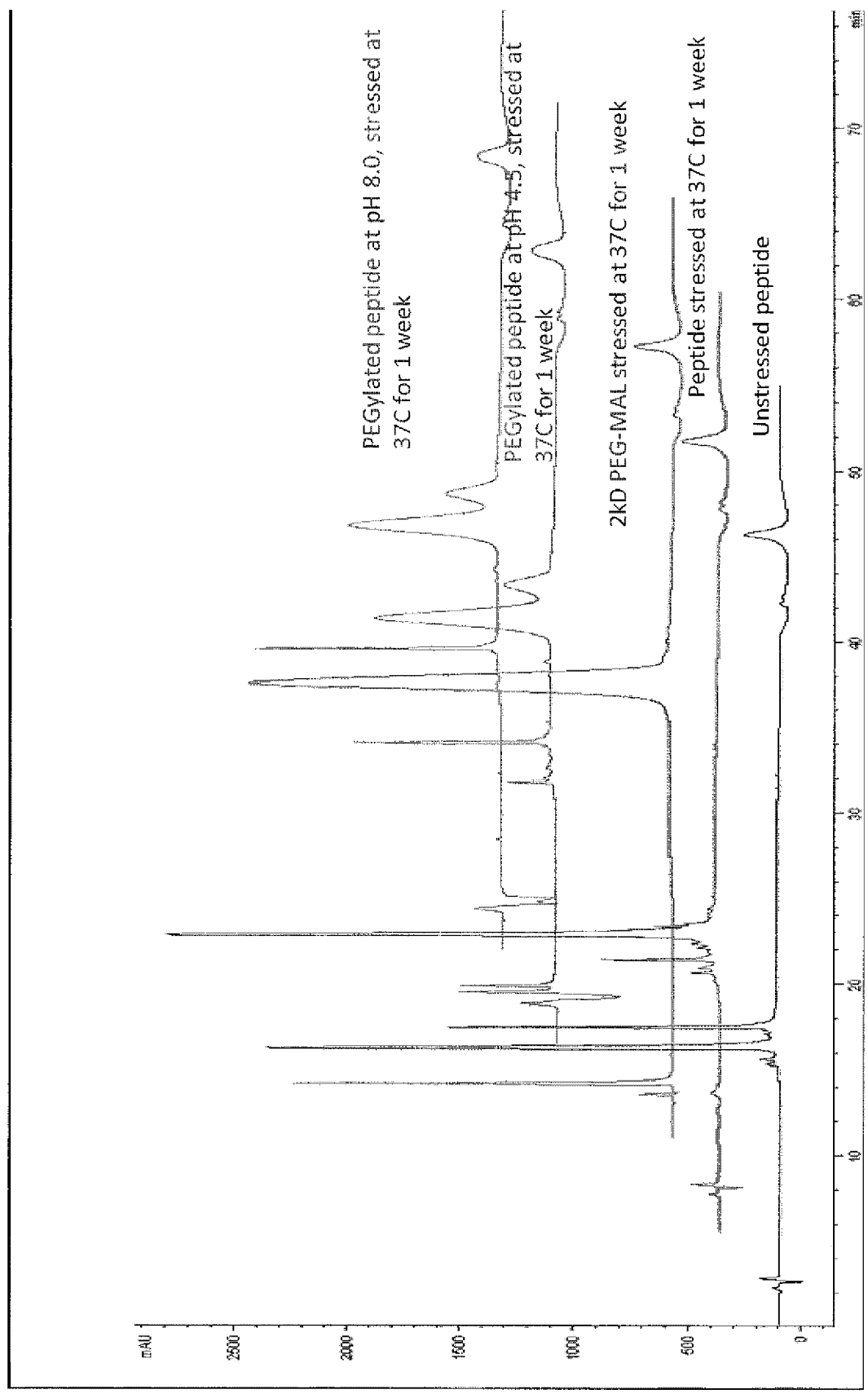
FIG. 16 shows HPLC profiles of samples of PEGylated peptides at pH 5.5 or pH 8.0 at T=0 or after 1 week at 37° C.

The results, which are shown in FIG. 16, indicate that, similarly to larger polypeptides, smaller peptides are subject to less dePEGylation at lower pH, compared to higher pH.

Example 7

Reduced DePEGylation of PEGylated Proteins at Lower pH Regardless of Type of PEG This Example shows that reducing the pH reduces dePEGylation of proteins regardless of whether they contain a large PEG, a small PEG, a branched PEG or a linear PEG.

C7 protein (SEQ ID NO: 48), was conjugated to a variety of PEG-MALs with different molecular weights, including 2 k, 5 k, 10 k, 12 k, 20 k, 20 k bis (bi-functional), 30 k and 40 k branched (NOF America Corp.). Each sample was purified over an ion-exchange column, then formulated in 50 mM sodium acetate at pH 4.5 or 50 mM Tris at pH 8.0. The samples were heat stressed at 37° C. for one week and the results were measured by RP-HPLC using a Jupiter C18 column (4.6*250 mm, PHENOMENEX®). The protein fragments were quantified on a relative percent basis to the intact sample at 280 nm using UV detection. The method utilizes a water/acetonitrile/trifluoroacetic acid gradient. For peak identification, LC-MS was conducted.

Figure 17:
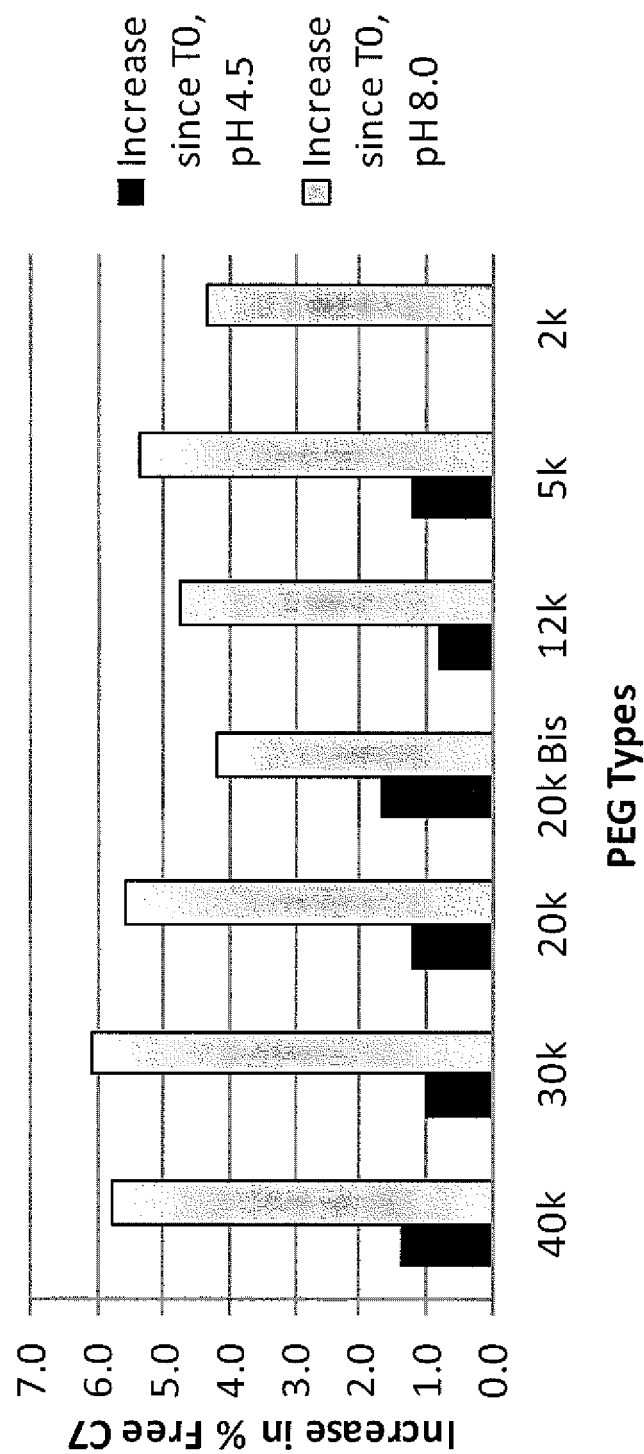
FIG. 17 is a histogram showing the increased percentage of free C7 protein derived from PEGylated C7 proteins after one week of heat stress of the PEGylated C7 proteins at 37° C. relative to T0, comparing samples formulated in pH 4.5 sodium acetate and pH 8.0 Tris.

The results, which are shown in FIG. 17, indicate a substantially higher level of dePEGylation after the heat stress in the samples at pH 8.0 relative to the samples at pH 5.5. In addition, the results also indicate no difference in the level of degradation among the different sizes of PEG-MALs used in the conjugation.

Incorporation by Reference

The entire disclosure of each document cited (including patents, patent applications, journal articles, abstracts, laboratory manuals, books, GENBANK® Accession numbers, SWISS-PROT® Accession numbers, or other disclosures) in the Background, Detailed Description, Brief Description of the Drawings, and Examples is hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

SEQUENCES

Naturally occurring human $^{10}$Fn3

(SEQ ID NO: 1)
VSDVPRDLEVVAAT<u>PTSLLI</u>SWDAPAVTVRYYRITYGE<u>TGGNS</u>PVQEFTV
PGSKST ATI<u>SGLKPG</u>VDYTITVYAVTGRGDSPASSKPISINYRT

Full length wild-type human $^{10}$Fn3 domain (SEQ ID NO: 47)
VSDVPRDLEVVAAT<u>PTSLLI</u>SWDAPAVTVRYYRITYGE<u>TGGNS</u>PVQEFTV
PGSKST ATI<u>SGLKPG</u>VDYTITVYAVTGRGDSPASSKPISINYRTEIDKP
SQ Antibody-like protein based on the $^{10}$Fn3 scaffold (SEQ ID NO: 2)
EVVAAT(X)$_a$<u>SLLI</u>(X)$_x$<u>YYRITYGE</u>(X)$_b$<u>QEFTV</u>(X)$_y$<u>ATI</u>(X)$_c$
<u>DYTITVYAV</u>(X)$_z$<u>ISINYRT</u>

Antibody-like protein based on the $^{10}$Fn3 scaffold (SEQ ID NO: 3)
EVVAATPTSLLI(X)$_x$<u>YYRITYGETGGNSPVQEFTV</u>(X)$_y$
ATISGLKPGVDYTITVYAV(X)$_z$<u>ISINYRT</u>

V core (SEQ ID NO: 4)
EVVAATPTSLLISWRHPHFPTRYYRITYGETGGNSPVQEFTVPLQPPTAT
ISGLKPGVDYTITVYAVTDGRNGRLLSIPISINYRT Full length FBSP-V (SEQ ID NO: 48)
GEVVAATPTSLLISWRHPHFPTRYYRITYGETGGNSPVQEFTVPLQPPTA
TISGLKPGVDYTITVYAVTDGRNGRLLSIPISINYRTEIDKPCQ Short Tail (SEQ ID NO: 5)
EIEK VEGFR2 BC Loop (SEQ ID NO: 6)
RHPHFPT VEGFR2 DE Loop (SEQ ID NO: 7)
LQPP VEGFR2 FG Loop (SEQ ID NO: 8)
DGRNGRLLSI

| SEQUENCES |
|---|
| DK+ VEGFR2/IGF-IR Binder<br>(SEQ ID NO: 9)<br>MGVSDVPRDLEVVAATPTSLLISWSARLKVARYYRITYGETGGNSPVQEF<br>TVPKNVYTATISGLKPGVDYTITVYAVTRFRDYQPISINYRTEIDKPSTS<br>TSTVSDVPRDLEVVAATPTSLLISWRHPHFPTRYYRITYGETGGNSPVQE<br>FTVPLQPPTATISGLKPGVDYTITVYAVTDGRNGRLLSIPISINYRTEID<br>KPCQ |
| Modified Cys Tail<br>(SEQ ID NO: 10)<br>EGSGC |
| Cys Tail<br>(SEQ ID NO: 11)<br>EIEKPCQ |
| (SEQ ID NO: 12)<br>EIEKPC |
| (SEQ ID NO: 13)<br>VSDVPRDLEVVAATPTSLLISWDAPAVTVRYYRITYGETGGNSPVQEFTV<br>PGSKSTATISGLKPGVDYTITVYAVTGRGDSPASSKPISINYRT |
| Extension sequence<br>(SEQ ID NO: 14)<br>EIDKPSQ |
| I core<br>(SEQ ID NO: 15)<br>EVVAATPTSLLISWSARLKVARYYRITYGETGGNSPVQEFTVPKNVYTAT<br>ISGLKPGVDYTITVYAVTRFRDYQPISINYRT |
| Extension sequence<br>(SEQ ID NO: 16)<br>EIDKPSQLE |
| (SEQ ID NO: 17)<br>MGVSDVPRDL |
| (SEQ ID NO: 18)<br>VSDVPRDL |
| (SEQ ID NO: 19)<br>GVSDVPRDL |
| (SEQ ID NO: 20)<br>$X_n$SDVPRDL, wherein n = 0, 1 or 2 amino acids,<br>wherein when n = 1, X is Met or Gly, and when<br>n = 2, X is Met-Gly |
| (SEQ ID NO: 21)<br>$X_n$DVPRDL, wherein n = 0, 1 or 2 amino acids,<br>wherein when n = 1, X is Met or Gly, and when<br>n = 2, X is Met-Gly |
| (SEQ ID NO: 22)<br>$X_n$VPRDL, wherein n = 0, 1 or 2 amino acids,<br>wherein when n = 1, X is Met or Gly, and when<br>n = 2, X is Met-Gly |
| (SEQ ID NO: 23)<br>$X_n$PRDL, wherein n = 0, 1 or 2 amino acids,<br>wherein when n = 1, X is Met or Gly, and when<br>n = 2, X is Met-Gly |
| (SEQ ID NO: 24)<br>$X_n$RDL, wherein n = 0, 1 or 2 amino acids,<br>wherein when n = 1, X is Met or Gly, and when<br>n = 2, X is Met-Gly |
| (SEQ ID NO: 25)<br>$X_n$DL, wherein n = 0, 1 or 2 amino acids,<br>wherein when n = 1, X is Met or Gly, and when<br>n = 2, X is Met-Gly |
| (SEQ ID NO: 26)<br>EIEKPSQ |
| (SEQ ID NO: 27)<br>EIEKP |
| (SEQ ID NO: 28)<br>EIEKPS |
| (SEQ ID NO: 29)<br>EIDK |
| (SEQ ID NO: 30)<br>EIDKPCQ |
| Fn linker<br>(SEQ ID NO: 31)<br>PSTSTST |
| $GS_5$ linker<br>(SEQ ID NO: 32)<br>GSGSGSGSGS |
| $GS_{10}$ linker<br>(SEQ ID NO: 33)<br>GSGSGSGSGSGSGSGSGSGS |
| $(GGGGS)_3$<br>(SEQ ID NO: 34)<br>GGGGS GGGGS GGGGS |
| $(GGGGS)_5$<br>(SEQ ID NO: 35)<br>GGGGS GGGGS GGGGS GGGGS GGGGS |
| $G_4SG_4SG_3SG$<br>(SEQ ID NO: 36)<br>GGGGSGGGGSGGGSG |
| (SEQ ID NO: 37)<br>GPG |
| (SEQ ID NO: 38)<br>GPGPGPG |
| (SEQ ID NO: 39)<br>GPGPGPGPGPG |
| PA3 linker<br>(SEQ ID NO: 40)<br>PAPAPA |
| PA6 linker<br>(SEQ ID NO: 41)<br>PAPAPAPAPAPA |
| PA9 linker<br>(SEQ ID NO: 42)<br>PAPAPAPAPAPAPAPAPA |
| E Core<br>(SEQ ID NO: 43)<br>EVVAATPTSLLISWWAPVDRYQYYRITYGETGGNSPVQEFTVPRDVYTAT<br>ISGLKPGVDYTITVYAVTDYKPHADGPHTYHESPISINYRT |
| IGF-IR BC Loop<br>(SEQ ID NO: 44)<br>SARLKVA |

| SEQUENCES | |
|---|---|
| IGF-IR DE Loop | (SEQ ID NO: 45) |
| KNVY | |
| IGF-IR FG Loop | (SEQ ID NO: 46) |
| RFRDYQ | |

| SEQUENCES | |
|---|---|
| TEIEKPCQ | (SEQ ID NO: 49) |
| TEIDKPCQ | (SEQ ID NO: 50) |

We claim:

1. A method for maintaining PEGylation of polypeptides comprising a tenth fibronectin type III ($^{10}$Fn3) domain during storage, the method comprising storing the polypeptides in a solution buffered to a pH between pH 2.0 and pH 4.5, wherein the polypeptides are conjugated to a polyethylene glycol (PEG) moiety through a maleimide linker via site-directed PEGylation to a cysteine residue of the polypeptide, wherein less than 5% of the maleimide linkers are cleaved over a four week storage period, and wherein the C-terminal tail of the $^{10}$Fn3 domain does not contain a DK sequence.

2. The method of claim 1, wherein less than 5% of the maleimide linkers are cleaved over an eight week storage period.

3. The method of claim 1, wherein the $^{10}$Fn3 domain has an altered amino acid sequence relative to the wild-type sequence that binds to a target molecule with a $K_D$ of less than 500 nM.

4. The method of claim 1, wherein the PEG moiety is attached to the cysteine residue on the C-terminal tail of the $^{10}$Fn3 domain.

5. The method of claim 4, wherein the maleimide linker forms a thioether bond with a sulfhydryl group on the cysteine residue of the polypeptide.

6. The method of claim 1, wherein the pH of the solution is between 3.0 and 4.0.

7. The method of claim 1, wherein the pH of the solution is between 3.5 and 4.5.

8. The method of claim 1, wherein the concentration of the PEGylated polypeptides in the solution is from 1-10 mg/mL.

9. The method of claim 1, wherein the PEGylated polypeptides are stored at a temperature from 4° C. to 30° C.

10. The method of claim 1, wherein the buffer lacks sodium chloride.

11. The method of claim 1, wherein the buffer is selected from the group consisting of: (a) 25 mM succinate and 5% sorbitol and (b) 10 mM sodium acetate and 5% mannitol.

* * * * *

SEQUENCE LISTING

<160> NUMBER OF SEQ ID NOS: 52

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 157
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(21)
<223> OTHER INFORMATION: Any amino acid and this region may encompass
      1-15, 2-15, 1-10, 2-10, 1-8, 2-8, 1-5, 2-5, 1-4, 2-4, 1-3, 2-3 or
      1-2 residues, wherein some positions may be absent
<220> FEATURE:
<221> NAME/KEY: MOD_RES
<222> LOCATION: (26)..(45)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7 or 6-7 residues, wherein some positions may be
      absent
<220> FEATURE:
<221> NAME/KEY: MOD_RES
<222> LOCATION: (54)..(73)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7 or 6-7 residues, wherein some positions may be
      absent
<220> FEATURE:
<221> NAME/KEY: MOD_RES
<222> LOCATION: (79)..(98)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7 or 6-7 residues, wherein some positions may be
      absent
<220> FEATURE:
<221> NAME/KEY: MOD_RES
<222> LOCATION: (102)..(121)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7 or 6-7 residues, wherein some positions may be
     absent
<220> FEATURE:
<221> NAME/KEY: MOD_RES
<222> LOCATION: (131)..(150)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7 or 6-7 residues, wherein some positions may be
     absent
<220> FEATURE:
<223> OTHER INFORMATION: see specification as filed for detailed
     description of substitutions and preferred embodiments

<400> SEQUENCE: 2

Glu Val Val Ala Ala Thr Xaa Xaa Xaa Xaa Xaa Xaa Xaa Xaa Xaa
1               5                   10                  15

Xaa Xaa Xaa Xaa Xaa Ser Leu Leu Ile Xaa Xaa Xaa Xaa Xaa Xaa
                20                  25                  30

Xaa Xaa Xaa Xaa Xaa Xaa Xaa Xaa Xaa Xaa Xaa Tyr Tyr Arg
            35                  40                  45

Ile Thr Tyr Gly Glu Xaa Xaa Xaa Xaa Xaa Xaa Xaa Xaa Xaa Xaa
    50                  55                  60

Xaa Xaa Xaa Xaa Xaa Xaa Xaa Xaa Gln Glu Phe Thr Val Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Ala Thr Ile Xaa Xaa Xaa Xaa Xaa Xaa Xaa Xaa Xaa Xaa
                100                 105                 110

Xaa Xaa Xaa Xaa Xaa Xaa Xaa Xaa Xaa Asp Tyr Thr Ile Thr Val Tyr
        115                 120                 125

Ala Val Xaa Xaa Xaa Xaa Xaa Xaa Xaa Xaa Xaa Xaa Xaa Xaa Xaa
    130                 135                 140

Xaa Xaa Xaa Xaa Xaa Xaa Ile Ser Ile Asn Tyr Arg Thr
145                 150                 155

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
     polypeptide
<220> FEATURE:
<221> NAME/KEY: MOD_RES
<222> LOCATION: (13)..(32)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7 or 6-7 residues, wherein some positions may be
     absent
<220> FEATURE:
<221> NAME/KEY: MOD_RES
<222> LOCATION: (53)..(72)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7 or 6-7 residues, wherein some positions may be
     absent
<220> FEATURE:
<221> NAME/KEY: MOD_RES
<222> LOCATION: (92)..(111)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7 or 6-7 residues, wherein some positions may be
     absent
<220> FEATURE:
<223> OTHER INFORMATION: see specification as filed for detailed description of substitutions and preferred embodiments

<400> SEQUENCE: 3

Glu Val Val Ala Ala Thr Pro Thr Ser Leu Leu Ile Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Tyr Tyr Arg Ile Thr Tyr Gly Glu Thr Gly Gly Asn Ser Pro Val Gln
            35                  40                  45

Glu Phe Thr Val Xaa Xaa Xaa Xaa Xaa Xaa Xaa Xaa Xaa Xaa Xaa Xaa
50                  55                  60

Xaa Xaa Xaa Xaa Xaa Xaa Xaa Ala Thr Ile Ser Gly Leu Lys Pro
65                  70                  75                  80

Gly Val Asp Tyr Thr Ile Thr Val Tyr Ala Val Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Ile
            100                 105                 110

Ser Ile Asn Tyr Arg Thr
            115

<210> SEQ ID NO 4
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Val Ala Ala Thr Pro Thr Ser Leu Leu Ile Ser Trp Arg His
1               5                   10                  15

Pro His Phe Pro Thr Arg Tyr Tyr Arg Ile Thr Tyr Gly Glu Thr Gly
            20                  25                  30

Gly Asn Ser Pro Val Gln Glu Phe Thr Val Pro Leu Gln Pro Pro Thr
        35                  40                  45

Ala Thr Ile Ser Gly Leu Lys Pro Gly Val Asp Tyr Thr Ile Thr Val
50                  55                  60

Tyr Ala Val Thr Asp Gly Arg Asn Gly Arg Leu Leu Ser Ile Pro Ile
65                  70                  75                  80

Ser Ile Asn Tyr Arg Thr
                85

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ile Glu Lys
1

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 6

Arg His Pro His Phe Pro Thr
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Leu Gln Pro Pro
1

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Gly Arg Asn Gly Arg Leu Leu Ser Ile
1               5                   10

<210> SEQ ID NO 9
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Val Ser Asp Val Pro Arg Asp Leu Glu Val Val Ala Ala Thr
1               5                   10                  15

Pro Thr Ser Leu Leu Ile Ser Trp Ser Ala Arg Leu Lys Val Ala Arg
            20                  25                  30

Tyr Tyr Arg Ile Thr Tyr Gly Glu Thr Gly Gly Asn Ser Pro Val Gln
        35                  40                  45

Glu Phe Thr Val Pro Lys Asn Val Tyr Thr Ala Thr Ile Ser Gly Leu
    50                  55                  60

Lys Pro Gly Val Asp Tyr Thr Ile Thr Val Tyr Ala Val Thr Arg Phe
65                  70                  75                  80

Arg Asp Tyr Gln Pro Ile Ser Ile Asn Tyr Arg Thr Glu Ile Asp Lys
                85                  90                  95

Pro Ser Thr Ser Thr Ser Thr Val Ser Asp Val Pro Arg Asp Leu Glu
            100                 105                 110

Val Val Ala Ala Thr Pro Thr Ser Leu Leu Ile Ser Trp Arg His Pro
        115                 120                 125

His Phe Pro Thr Arg Tyr Tyr Arg Ile Thr Tyr Gly Glu Thr Gly Gly
    130                 135                 140

Asn Ser Pro Val Gln Glu Phe Thr Val Pro Leu Gln Pro Pro Thr Ala
145                 150                 155                 160

Thr Ile Ser Gly Leu Lys Pro Gly Val Asp Tyr Thr Ile Thr Val Tyr
                165                 170                 175

Ala Val Thr Asp Gly Arg Asn Gly Arg Leu Leu Ser Ile Pro Ile Ser
```

```
                180                 185                 190
Ile Asn Tyr Arg Thr Glu Ile Asp Lys Pro Cys Gln
        195                 200

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Gly Ser Gly Cys
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Glu Lys Pro Cys Gln
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Ile Glu Lys Pro Cys
1               5

<210> SEQ ID NO 13
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 14
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Ile Asp Lys Pro Ser Gln
1               5

<210> SEQ ID NO 15
<211> LENGTH: 82
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Val Ala Ala Thr Pro Thr Ser Leu Leu Ile Ser Trp Ser Ala
1               5                   10                  15

Arg Leu Lys Val Ala Arg Tyr Tyr Arg Ile Thr Tyr Gly Glu Thr Gly
                20                  25                  30

Gly Asn Ser Pro Val Gln Glu Phe Thr Val Pro Lys Asn Val Tyr Thr
            35                  40                  45

Ala Thr Ile Ser Gly Leu Lys Pro Gly Val Asp Tyr Thr Ile Thr Val
        50                  55                  60

Tyr Ala Val Thr Arg Phe Arg Asp Tyr Gln Pro Ile Ser Ile Asn Tyr
65                  70                  75                  80

Arg Thr

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu Ile Asp Lys Pro Ser Gln Leu Glu
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Gly Val Ser Asp Val Pro Arg Asp Leu
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Ser Asp Val Pro Arg Asp Leu
```

```
1               5
```

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gly Val Ser Asp Val Pro Arg Asp Leu
1               5
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be
      absent
<220> FEATURE:
<223> OTHER INFORMATION: see specification as filed for detailed
      description of substitutions and preferred embodiments

<400> SEQUENCE: 20

```
Xaa Xaa Ser Asp Val Pro Arg Asp Leu
1               5
```

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be
      absent
<220> FEATURE:
<223> OTHER INFORMATION: see specification as filed for detailed
      description of substitutions and preferred embodiments

<400> SEQUENCE: 21

```
Xaa Xaa Asp Val Pro Arg Asp Leu
1               5
```

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be absent
<220> FEATURE:
<223> OTHER INFORMATION: see specification as filed for detailed
      description of substitutions and preferred embodiments

```
<400> SEQUENCE: 22

Xaa Xaa Val Pro Arg Asp Leu
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be absent
<220> FEATURE:
<223> OTHER INFORMATION: see specification as filed for detailed
      description of substitutions and preferred embodiments

<400> SEQUENCE: 23

Xaa Xaa Pro Arg Asp Leu
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be absent
<220> FEATURE:
<223> OTHER INFORMATION: see specification as filed for detailed
      description of substitutions and preferred embodiments

<400> SEQUENCE: 24

Xaa Xaa Arg Asp Leu
1               5

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be absent
<220> FEATURE:
<223> OTHER INFORMATION: see specification as filed for detailed
      description of substitutions and preferred embodiments

<400> SEQUENCE: 25

Xaa Xaa Asp Leu
1

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 26

Glu Ile Glu Lys Pro Ser Gln
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Ile Glu Lys Pro
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Ile Glu Lys Pro Ser
1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Ile Asp Lys
1

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Ile Asp Lys Pro Cys Gln
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Pro Ser Thr Ser Thr Ser Thr
1               5

<210> SEQ ID NO 32
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Gly Ser Gly Ser Gly Ser Gly Ser
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser Gly Ser Gly Ser Gly Ser Gly Ser Gly Ser Gly Ser Gly Ser
1               5                   10                  15

Gly Ser Gly Ser
            20

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Gly Ser Gly Gly Gly Gly Ser Gly Gly Gly Gly Ser
1               5                   10                  15

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Gly Ser Gly Gly Gly Gly Ser Gly Gly Gly Ser Gly
1               5                   10                  15

<210> SEQ ID NO 37
<211> LENGTH: 3
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 37

Gly Pro Gly
1

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Pro Gly Pro Gly Pro Gly
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Pro Gly Pro Gly Pro Gly Pro Gly Pro Gly
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Ala Pro Ala Pro Ala
1               5

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Pro Ala Pro Ala Pro Ala Pro Ala Pro Ala Pro Ala
1               5                   10

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Ala Pro Ala Pro Ala Pro Ala Pro Ala Pro Ala Pro Ala Pro Ala
1               5                   10                  15

Pro Ala

<210> SEQ ID NO 43
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Val Ala Ala Thr Pro Thr Ser Leu Leu Ile Ser Trp Trp Ala
1               5                   10                  15

Pro Val Asp Arg Tyr Gln Tyr Tyr Arg Ile Thr Tyr Gly Glu Thr Gly
            20                  25                  30

Gly Asn Ser Pro Val Gln Glu Phe Thr Val Pro Arg Asp Val Tyr Thr
        35                  40                  45

Ala Thr Ile Ser Gly Leu Lys Pro Gly Val Asp Tyr Thr Ile Thr Val
    50                  55                  60

Tyr Ala Val Thr Asp Tyr Lys Pro His Ala Asp Gly Pro His Thr Tyr
65                  70                  75                  80

His Glu Ser Pro Ile Ser Ile Asn Tyr Arg Thr
                85                  90

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ala Arg Leu Lys Val Ala
1               5

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Asn Val Tyr
1

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Phe Arg Asp Tyr Gln
1               5

<210> SEQ ID NO 47
<211> LENGTH: 101
<212> TYPE: PRT
<213> ORGANISM: Homo sapiens

<400> SEQUENCE: 47

```
Val Ser Asp Val Pro Arg Asp Leu Glu Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 48
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Glu Val Val Ala Ala Thr Pro Thr Ser Leu Leu Ile Ser Trp Arg
1               5                   10                  15

His Pro His Phe Pro Thr Arg Tyr Tyr Arg Ile Thr Tyr Gly Glu Thr
                20                  25                  30

Gly Gly Asn Ser Pro Val Gln Glu Phe Thr Val Pro Leu Gln Pro Pro
            35                  40                  45

Thr Ala Thr Ile Ser Gly Leu Lys Pro Gly Val Asp Tyr Thr Ile Thr
        50                  55                  60

Val Tyr Ala Val Thr Asp Gly Arg Asn Gly Arg Leu Leu Ser Ile Pro
65                  70                  75                  80

Ile Ser Ile Asn Tyr Arg Thr Glu Ile Asp Lys Pro Cys Gln
                85                  90

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Glu Ile Glu Lys Pro Cys Gln
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Glu Ile Asp Lys Pro Cys Gln
1               5
```

```
<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Met, Gly or 'Met Gly,' wherein some positions may be absent
<220> FEATURE:
<223> OTHER INFORMATION: see specification as filed for detailed
      description of substitutions and preferred embodiments

<400> SEQUENCE: 51

Xaa Xaa Leu
1

<210> SEQ ID NO 52
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: This region may encompass 0-2 residues selected
      from Glu, Ile or 'Glu Ile,' wherein some positions may be absent
<220> FEATURE:
<221> NAME/KEY: misc_feature
<222> LOCATION: (3)..(22)
<223> OTHER INFORMATION: This region may encompass 2-10, 2-8, 2-5, 3-10,
      3-8, 3-7, 3-5, 4-7, 2, 3, 4, 5, 6, 7, 8, 9 or 10 'Glu Asp'
      repeating units, wherein some positions may be absent
<220> FEATURE:
<223> OTHER INFORMATION: see specification as filed for detailed
      description of substitutions and preferred embodiments

<400> SEQUENCE: 52

Xaa Xaa Glu Asp Glu Asp Glu Asp Glu Asp Glu Asp Glu Asp Glu Asp
1               5                   10                  15

Glu Asp Glu Asp Glu Asp
            20
```